US012637442B2

(12) United States Patent
Su et al.

(10) Patent No.: US 12,637,442 B2
(45) Date of Patent: May 26, 2026

(54) ORGANIC ELECTRONIC MATERIAL CONTAINING NITROGEN ATOM HETEROCYCLIC RING, PREPARATION METHOD THEREFOR AND APPLICATION THEREOF

(71) Applicant: SHANGHAI CHUANQIN NEW MATERIAL CO., LTD, Shanghai (CN)

(72) Inventors: Yan Su, Shanghai (CN); Haitao Zhou, Shanghai (CN); Zhuju Huang, Shanghai (CN)

(73) Assignee: SHANGHAI CHUANQIN NEW MATERIAL CO., LTD, Shanghai (CN)

( * ) Notice: Subject to any disclaimer, the term of this patent is extended or adjusted under 35 U.S.C. 154(b) by 865 days.

(21) Appl. No.: 17/789,539

(22) PCT Filed: Dec. 1, 2020

(86) PCT No.: PCT/CN2020/133181
§ 371 (c)(1),
(2) Date: Jun. 28, 2022

(87) PCT Pub. No.: WO2021/139452
PCT Pub. Date: Jul. 15, 2021

(65) Prior Publication Data

US 2023/0086539 A1 Mar. 23, 2023

(30) Foreign Application Priority Data

Jan. 8, 2020 (CN) ......................... 202010016693.9
Jan. 8, 2020 (CN) ......................... 202010016694.3
Feb. 4, 2020 (CN) ......................... 202010079875.0

(51) Int. Cl.
*H01L 51/00* (2006.01)
*C07D 401/10* (2006.01)
(Continued)

(52) U.S. Cl.
CPC ........... *C07D 401/10* (2013.01); *H10K 85/00* (2023.02); *H10K 85/654* (2023.02); *H10K 50/11* (2023.02);
(Continued)

(58) Field of Classification Search
None
See application file for complete search history.

(56) References Cited

FOREIGN PATENT DOCUMENTS

CN 107445910 A 12/2017
CN 108299388 A 7/2018
(Continued)

*Primary Examiner* — Jay Yang
(74) *Attorney, Agent, or Firm* — Hemisphere Law, PLLC

(57) ABSTRACT

The present disclosure provides an organic electronic material containing a nitrogen heterocycle and a preparation method and use thereof, and relates to the technical field of organic electroluminescence. Nitrogen-containing heterocycles such as pyridine, triazine or pyrimidine are introduced into a main structure of phenanthrene, such that the electronegativity of the material is enhanced, and the electron transport performance and the thermal stability of a compound are improved. The organic electron transport material provided by the present disclosure has a relatively good thermal stability, a high luminous efficiency and a high luminous purity. An organic light-emitting device prepared from the organic electronic material has effects of reducing a driving voltage, improving a luminous efficiency, enabling color purity to be excellent and prolonging a service life.

9 Claims, 6 Drawing Sheets

(51) Int. Cl.

| | |
|---|---|
| ***H10K 85/00*** | (2023.01) |
| ***H10K 85/60*** | (2023.01) |
| *H10K 50/11* | (2023.01) |
| *H10K 50/16* | (2023.01) |
| *H10K 50/17* | (2023.01) |
| *H10K 101/10* | (2023.01) |

(52) U.S. Cl.

CPC ........... *H10K 50/16* (2023.02); *H10K 50/171* (2023.02); *H10K 2101/10* (2023.02)

(56) References Cited

FOREIGN PATENT DOCUMENTS

| | | | |
|---|---|---|---|
| CN | 110114345 | A | 8/2019 |
| CN | 111170993 | | 5/2020 |
| CN | 111740020 | | 10/2020 |
| JP | 2009-221442 | A | 10/2009 |
| KR | 10-2011-0047803 | A | 5/2011 |

ORGANIC ELECTRONIC MATERIAL CONTAINING NITROGEN ATOM HETEROCYCLIC RING, PREPARATION METHOD THEREFOR AND APPLICATION THEREOF

TECHNICAL FIELD

The present disclosure belongs to the technical field of organic electroluminescence and specifically relates to an organic electronic material containing a nitrogen heterocycle and a preparation method and use thereof.

BACKGROUND

Along with development of science, technology and economy, requirements of people on the quality of life are also increased, of course, including display and lighting technologies closely related to the life of people. New display and lighting technologies need to meet color requirements of the human eyes and to be healthy and environmentally friendly. Organic light-emitting devices (OLEDs) are a new display technology. Since each pixel switches flexibly and the OLEDs actively emit light, display response time is short and degree of color contrast is high; a driving voltage is low and energy consumption can be reduced; an organic material enables the devices to be lighter, thinner and more environment-friendly; and a diversified selection of substrates provides possibility for a flexible and transparent display, thus the OLEDs are widely used in the fields of mobile phones, flat panel displays, televisions, illumination, vehicle-mounted display and the like.

The common OLEDs use a sandwich structure, namely an organic layer is sandwiched between an anode and a cathode at two sides. The organic layer is divided into a hole transport layer, an electron transport layer, a light-emitting layer, a hole blocking layer, an electron blocking layer and the like according to different photoelectric characteristics of various materials. A light-emitting mechanism of the devices is mainly as follows: under a drive of an external voltage, holes and electrons overcome energy barriers, are separately injected into the hole transport layer and the electron transport layer from an anode and a cathode, the holes and the electrons are compounded in the light-emitting layer, and an energy is released to be transferred to an organic light-emitting substance. The light-emitting substance receives the energy and transits from a ground state to an excited state. When an excited molecule transits to the ground state again, a light emits.

An electron transport material transports electrons on the cathode to the light-emitting layer. The electron transport material generally requires a better thermal stability and film-forming property, a higher electron mobility, a greater electron affinity and a higher excited state energy level.

Most organic electroluminescent materials transport holes faster than electrons. Therefore, the numbers of the electrons and the holes in the light-emitting layer are imbalanced, the devices are far from the light-emitting layer when emit light and close to an electrode, thus a higher driving voltage is required and efficiency and service life of the devices are also reduced. Recently, although the OLEDs have been gradually improved, materials having a better luminous efficiency, driving voltage, lifespan, etc. are required. Therefore, the electron transport material with a good thermal stability and an excellent performance is required to be developed.

SUMMARY

The present disclosure aims to provide an organic electronic material containing a nitrogen heterocycle and a preparation method and use thereof. In order to solve the problem, nitrogen-containing heterocycles such as pyridine, triazine or pyrimidine are introduced into a main structure of phenanthrene, such that electronegativity of the material is enhanced, and an electron transport performance and a thermal stability of a compound are improved. The present disclosure provides an organic electroluminescent compound with a high thermal stability, film-forming property and strong electron mobility. An organic light-emitting device prepared from the organic electronic material has an excellent luminous efficiency and a longer service life.

One aspect of the present disclosure provides an organic electronic material containing a nitrogen heterocycle, where the organic electronic material contains a compound of the following structural formula (I) or (II):

formula (I)

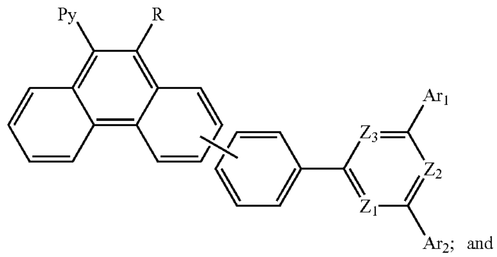

; and formula (II)

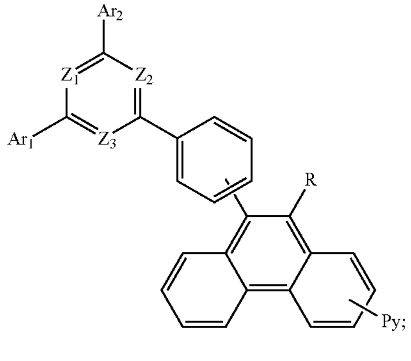

;

and wherein Py is substituted or unsubstituted $C_5$-$C_{30}$ pyridine;

R is hydrogen, $C_1$-$C_4$ alkyl, and substituted or unsubstituted $C_6$-$C_{30}$ aryl;

$Ar_1$ and $Ar_2$ are independently selected from substituted or unsubstituted $C_6$-$C_{30}$ aryl; and at least, one of $Z_1$, $Z_2$ and $Z_3$ is N and the others are CH.

Preferably, R may be independently selected from the group consisting of hydrogen, phenyl, tolyl, biphenyl, or naphthyl; and $Ar_1$ and $Ar_2$ are independently selected from the group consisting of phenyl, tolyl, biphenyl, naphthyl, phenanthryl, anthracyl, perylenyl, phenylnaphthyl, naphthylphenyl, diphenylphenyl, 9,9-dimethylfluorenyl, 9,9-diphenylfluorenyl, 9,9-spirobifluorenyl, dibenzofuranyl, dibenzothienyl, or benzophenanthryl.

Furthermore, preferably, Py may be a pyridyl, R may be a phenyl, and $Ar_1$ and $Ar_2$ may be independently selected from the group consisting of phenyl, biphenyl or naphthyl.

More preferably, the organic electronic material may include but be not limited to any one of the following compounds CQ1-CQ28:
CQ 1
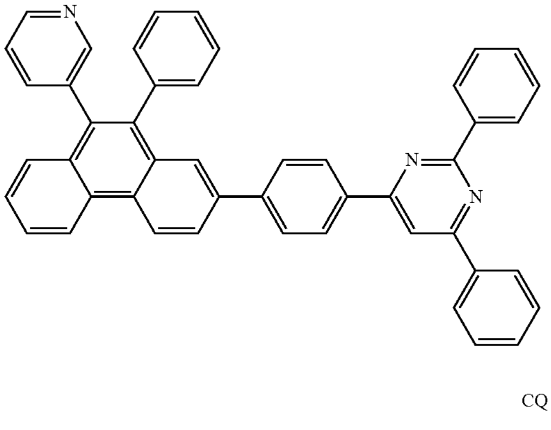
CQ 2
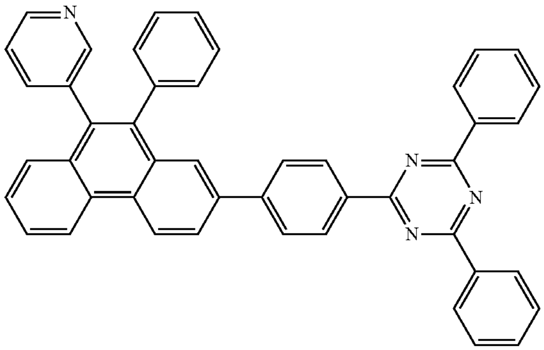
CQ 3
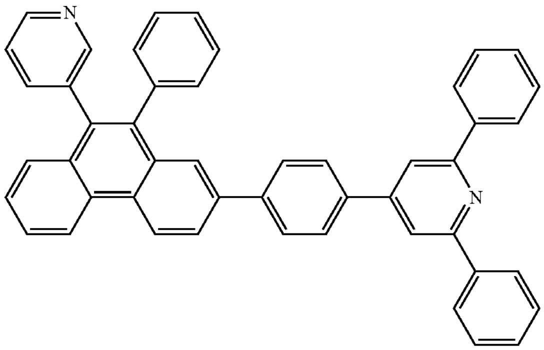
CQ 4
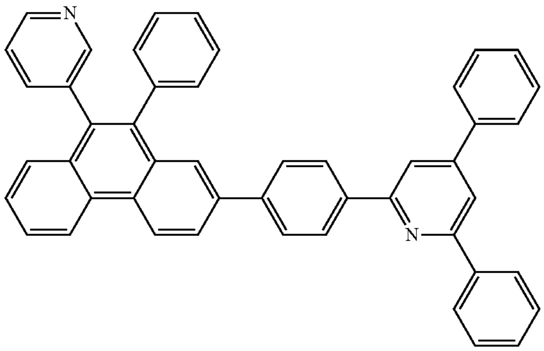
-continued
CQ 5
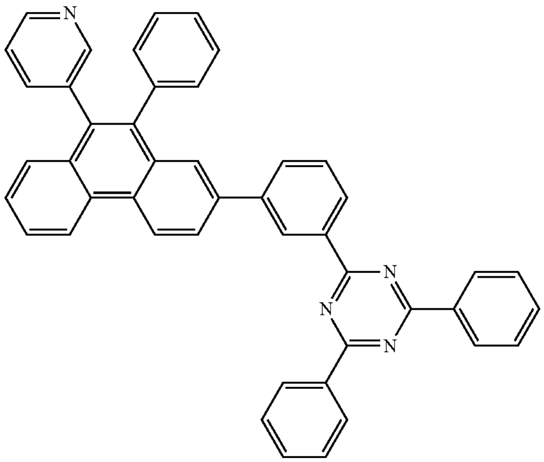
CQ 6
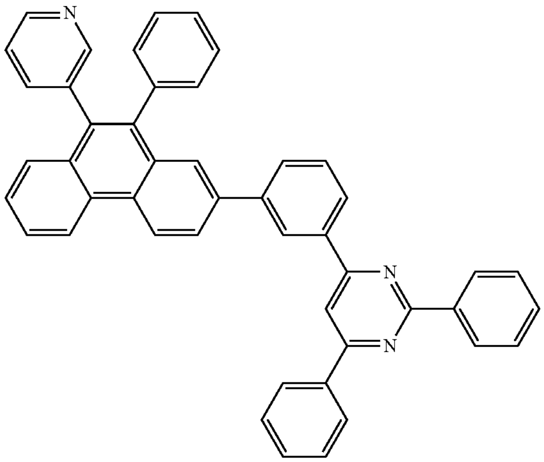
CQ 7
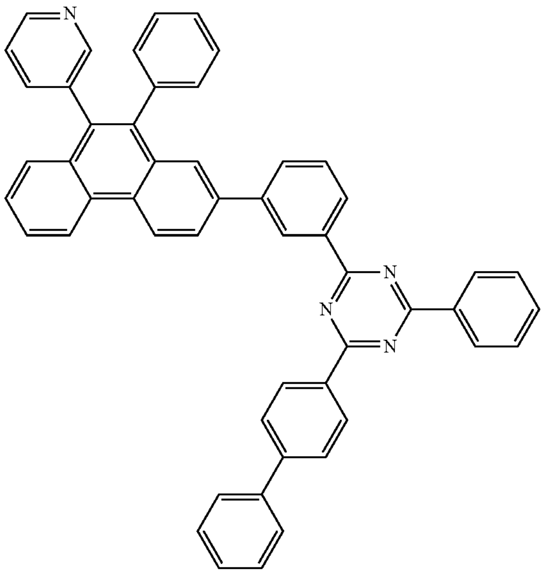

-continued
CQ 8
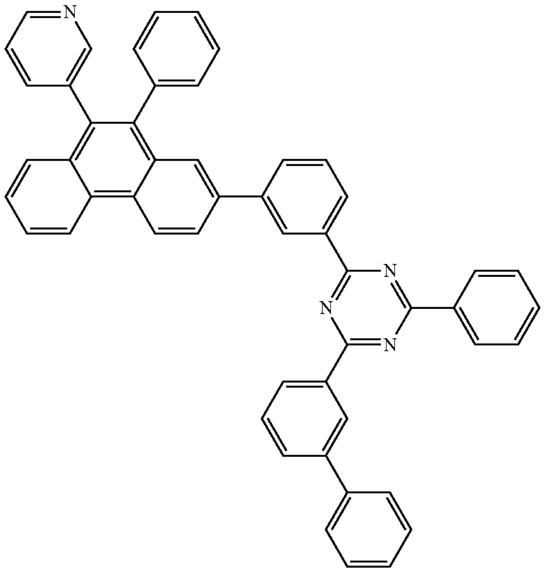
CQ 9
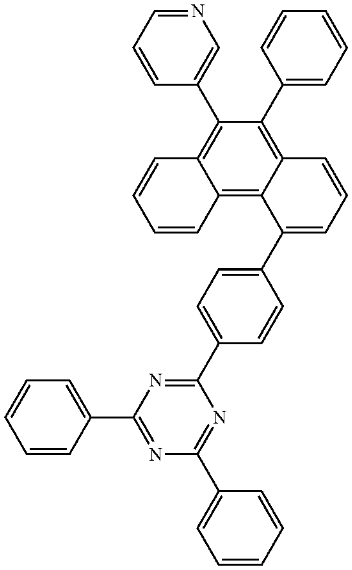
-continued
CQ 10
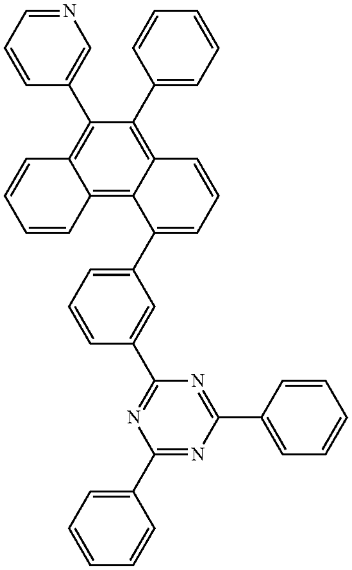
CQ 11
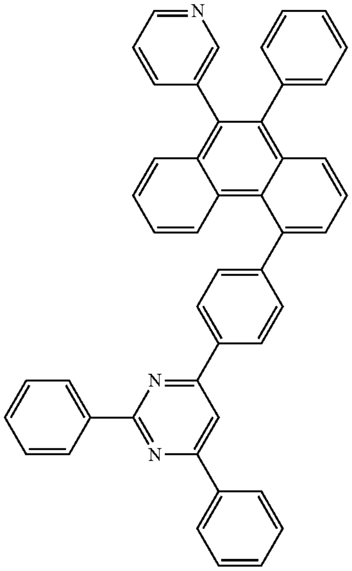

-continued
CQ 12
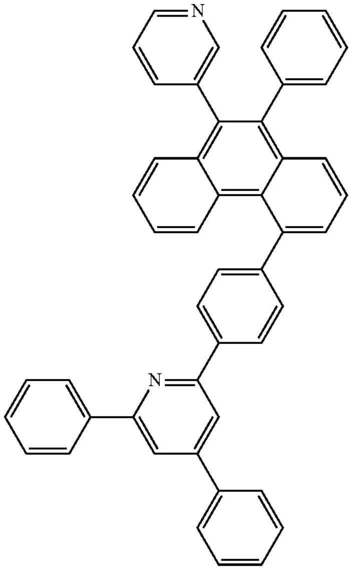
CQ 13
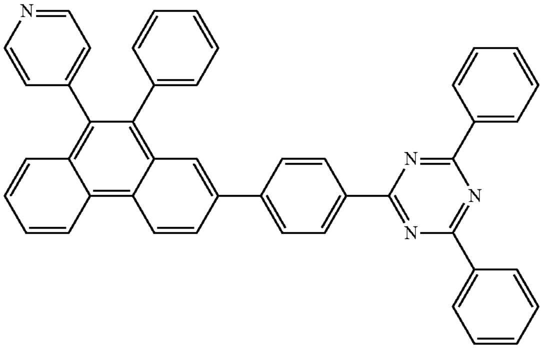
CQ 14
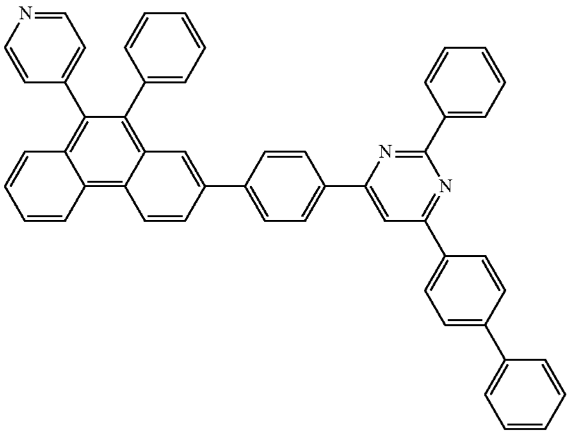
-continued
CQ 15
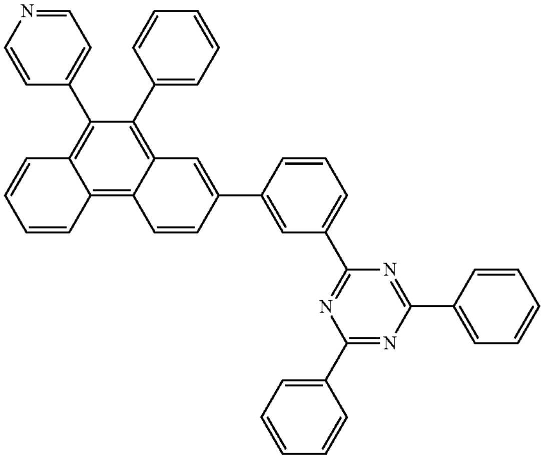
CQ 16
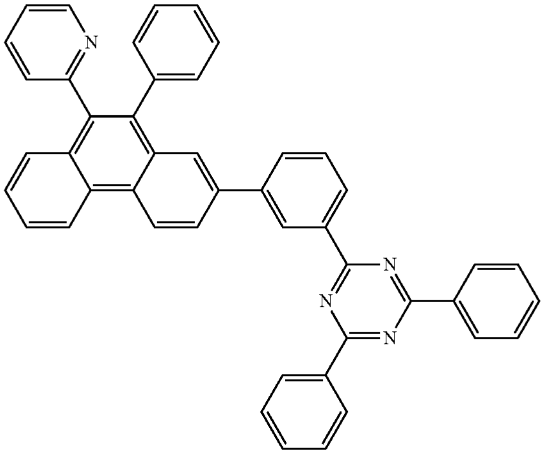
CQ 17
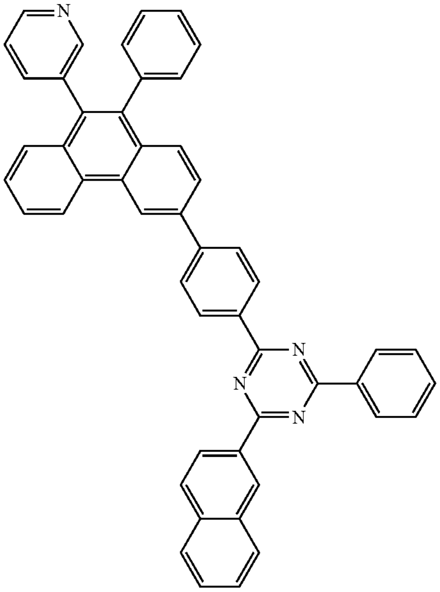

-continued
CQ 18
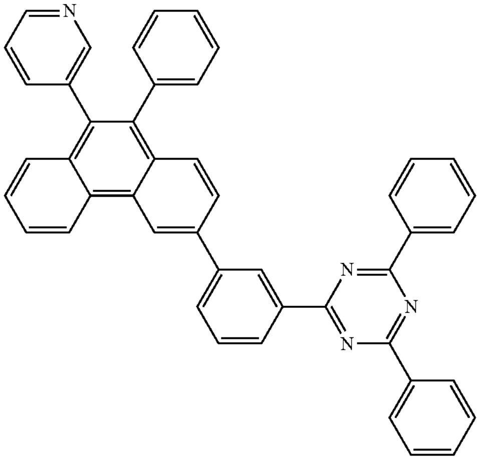
CQ 19
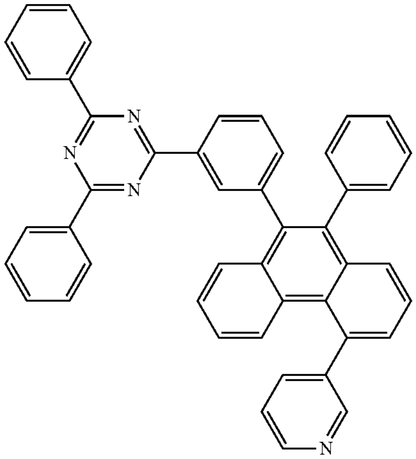
CQ 20
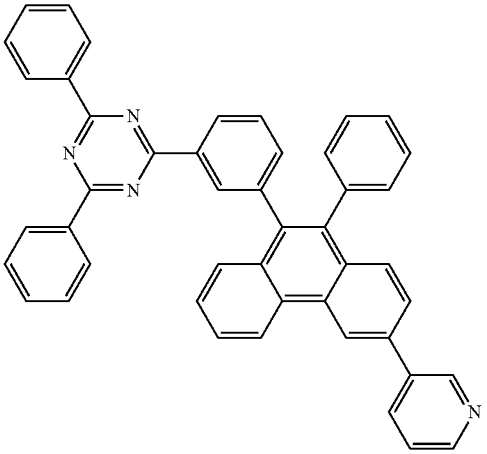
-continued
CQ 21
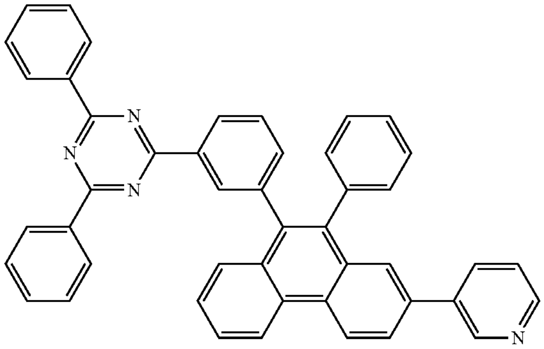
CQ 22
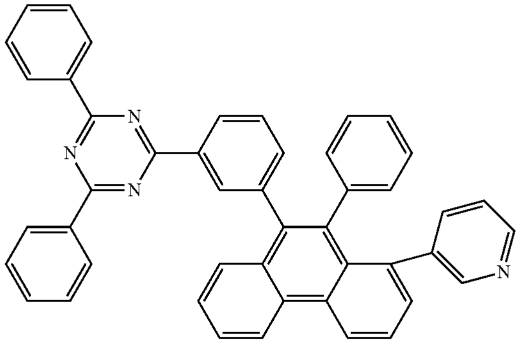
CQ 23
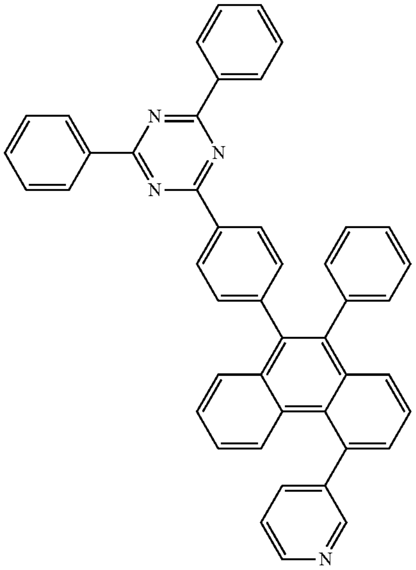

-continued

CQ 24

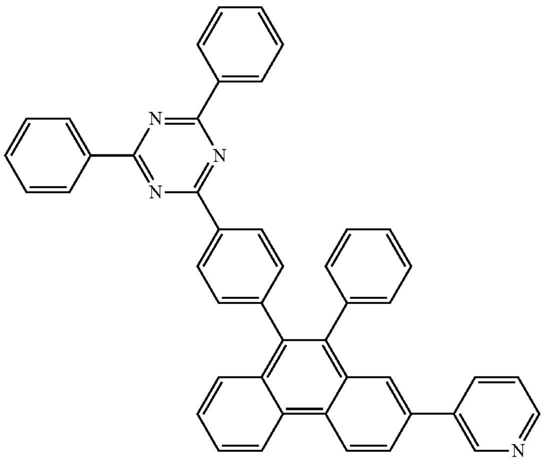

CQ 25

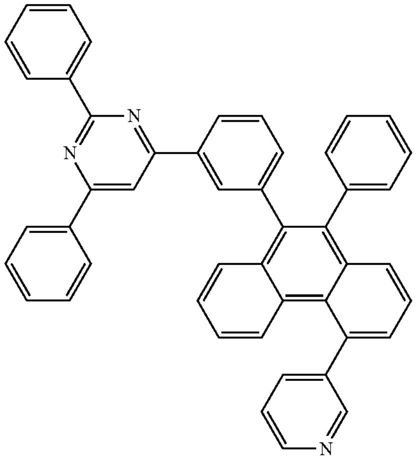

CQ 26

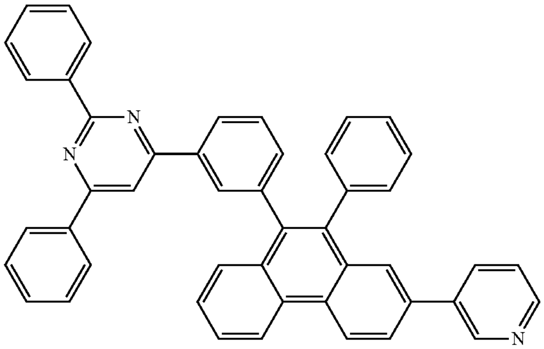

CQ 27

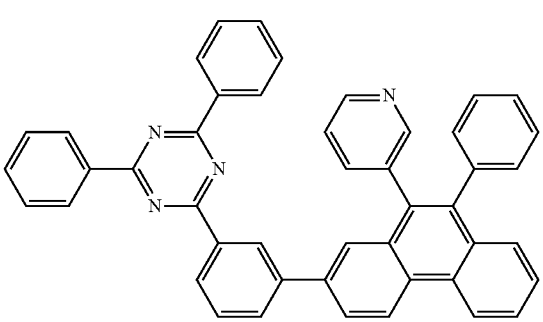

-continued

CQ 28

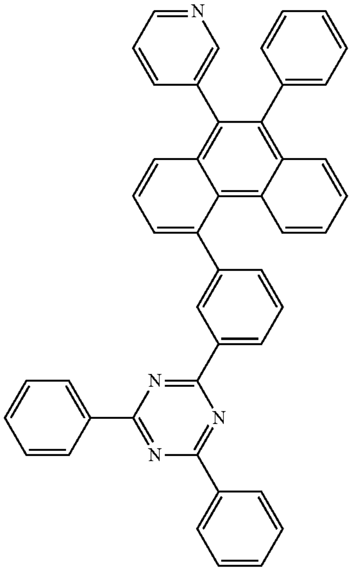

The present disclosure also provides a method for preparing the compound of structural formula (I) or (II), including the following steps:

(A1) synthesis of compound b: preparing compound b by a Sonogashira reaction of o-bromoiodobenzene with an alkynyl compound;

(A2) synthesis of compound c: preparing compound c by a Suzuki reaction of compound b with halogenated phenylboronic acid;

(A3) synthesis of compound d: preparing compound d by reacting compound c with iodine chloride or bromosuccinimide, where a solvent is dichloromethane, chloroform, tetrahydrofuran, 1,2-dichloroethane, acetonitrile, N,N-dimethylformamide, N,N-dimethylacetamide or dioxane;

(A4) synthesis of compound f: obtaining compound f by a Suzuki reaction of compound d and pyridinylboronic acid e or a pyridinylboronic ester; and (A5) synthesis of compound of structural formula (I): obtaining compound of structural formula (I) by a Suzuki reaction of compound j with boronate ester h;

or;

(B1) synthesis of compound b: preparing compound b by a Sonogashira reaction of o-bromoiodobenzene with an alkynyl compound;

(B2) synthesis of compound c: preparing compound c by a Suzuki reaction of compound b with halogenated phenylboronic acid;

(B3) synthesis of compound d: in a reaction of step 3, preparing compound d by reacting compound c with iodine chloride or bromosuccinimide, where a solvent is dichloromethane, chloroform, tetrahydrofuran, 1,2-dichloroethane acetonitrile, N,N-dimethylformamide, N,N-dimethylacetamide or dioxane;

(B4) synthesis of compound j: obtaining compound j by a Suzuki reaction of compound d and boronate ester h; and (B5) synthesis of compound of structural formula (II): obtaining compound of structural formula (II) by a Suzuki reaction of compound j with pyridinylboronic acid e or a pyridinylboronic ester;

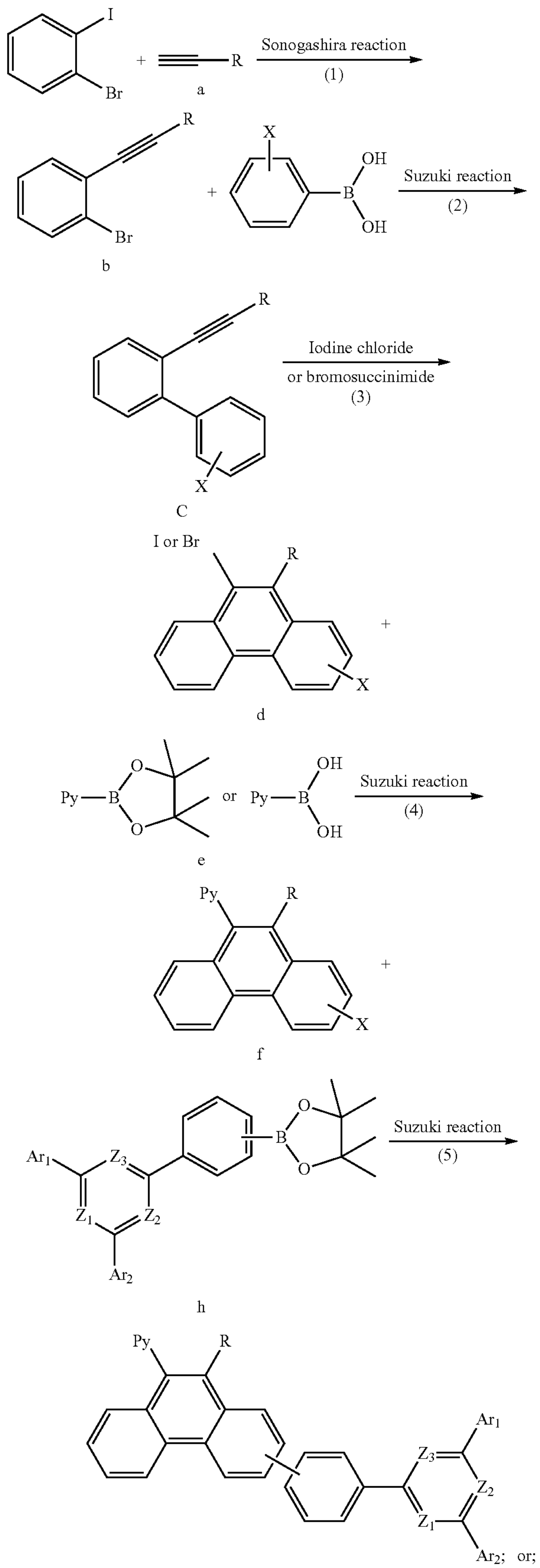

I or;

-continued

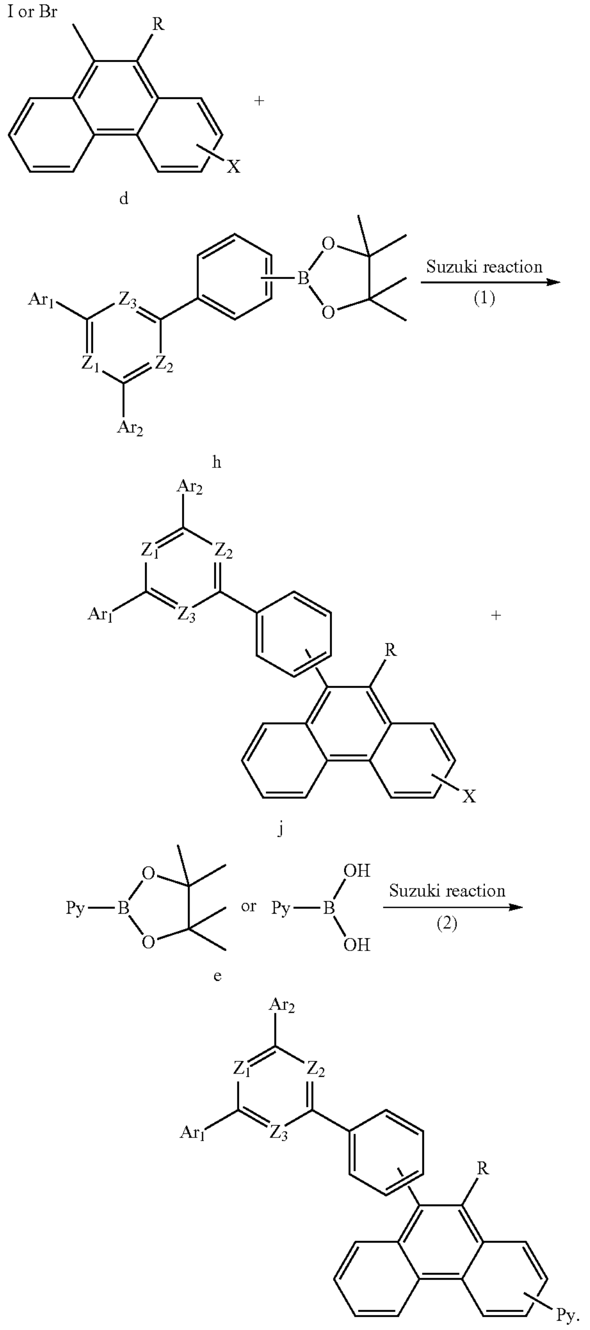

II

The raw materials of the compounds of the present disclosure are commercially available. In the above reaction formulas, definitions of R, Py, $Ar_1$, $Ar_2$, $Z_1$, $Z_2$ and $Z_3$ are the same as those described above, and X represents chlorine or bromine.

Another aspect of the present disclosure provides an organic light-emitting device, where the organic light-emitting device includes an anode, a cathode and an organic layer;

the organic layer includes one or more than one of a light-emitting layer, a hole injection layer, a hole transport layer, a hole blocking layer, an electron injection layer or an electron transport layer; and at least one of the organic layer comprises the organic electronic material.

Preferably, the light-emitting layer in the organic layer may include the organic electronic material.

Preferably, the electron transport layer or the electron injection layer in the organic layer may include the organic electronic material.

Preferably, the hole blocking layer in the organic layer may include the organic electronic material.

Preferably, the organic layer may have a total thickness of 1-1,000 nm; and further preferably, the organic layer may have a total thickness of 50-500 nm.

When the compound with structural formula I or II is used in the organic light-emitting device, other materials such as a hole injection layer, a hole transport layer, alight-emitting layer, an electron transport layer, an electron injection layer, a blocking layer and the like can, be matched to obtain blue light, green light, yellow light, red light or white light.

Each, organic layers in the organic light-emitting device of the present disclosure may be prepared by vacuum evaporation, molecular beam evaporation, dip coating in a solvent, spin coating, rod coating, inkjet printing, etc. A metal electrode can be prepared by evaporation or sputtering.

Another aspect of the present disclosure also provides use of the organic electronic material, where the organic electronic material is usable for producing an organic light-emitting device, an organic solar cell, an organic thin film transistor, an organic photodetector, an organic field effect transistor, an organic integrated circuit, an organic photoreceptor, etc.

Beneficial Effects of the Present Disclosure

The present disclosure provides an organic electronic material containing a nitrogen heterocycle and a preparation method and use thereof. The organic electronic material provided by the present disclosure has a relatively good thermal stability, a high luminous efficiency and a high luminous purity. An organic light-emitting device prepared from the organic electroluminescent compound has effects of reducing a driving voltage, improving a luminous efficiency, enabling color purity to be excellent and prolonging a service life.

Figure 4:
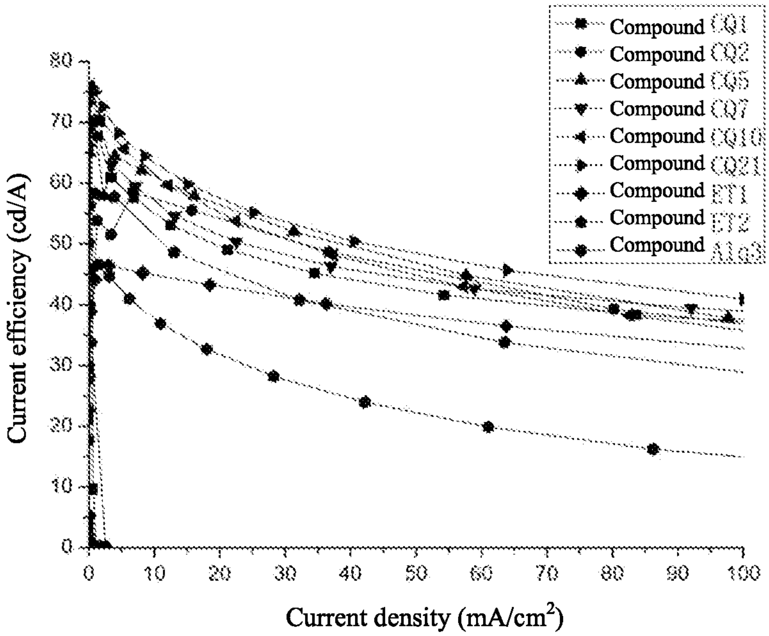
Figure 5:
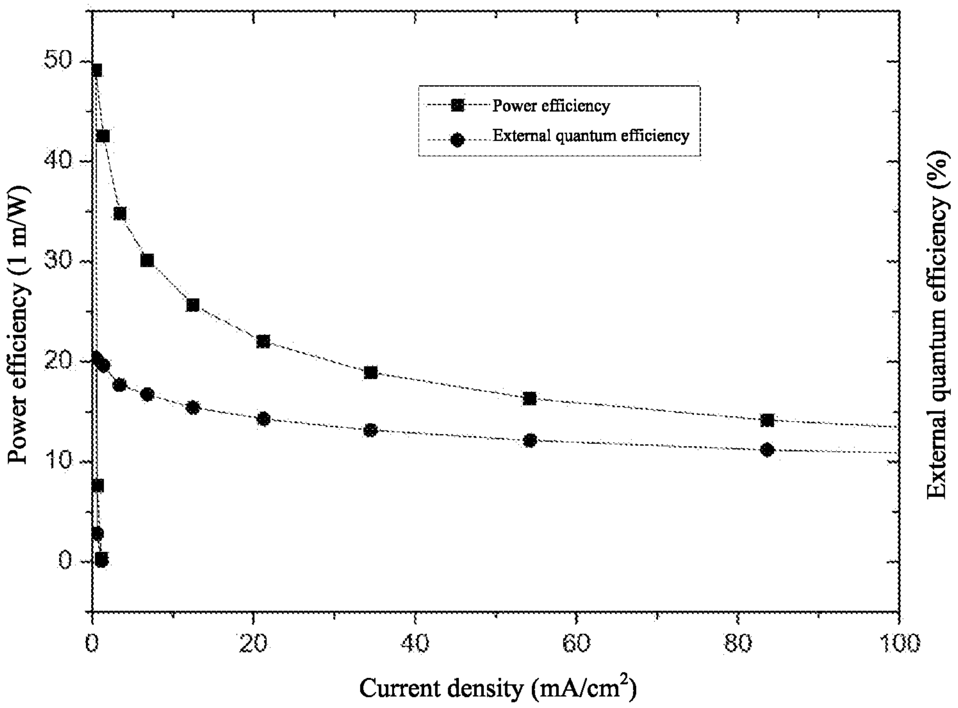
Figure 6:
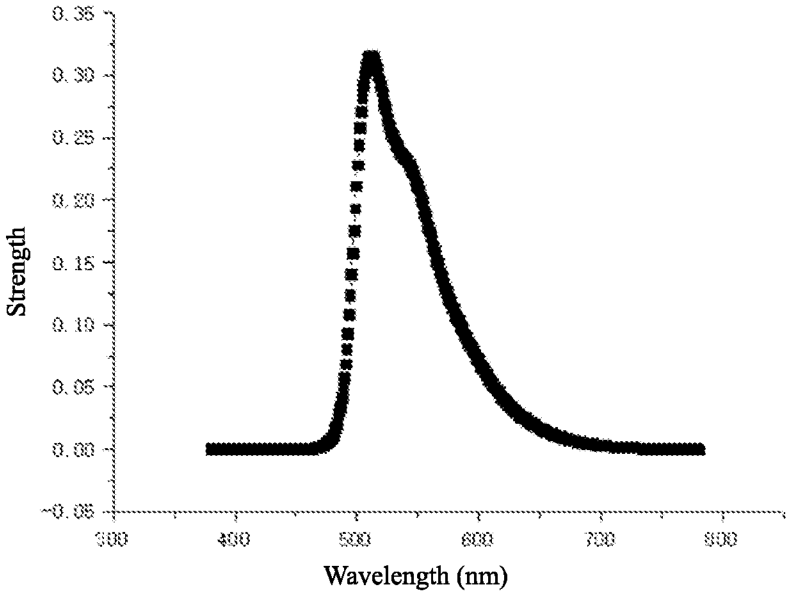

110, glass substrate; 120, anode; 130, hole injection layer; 140, hole transport layer; 150, blocking layer; 160, light-emitting layer; 170, electron transport layer; 180, electron injection layer; and 190, cathode;

FIG. 4 is a graph showing a correlation between a current density and a current efficiency of the device;

FIG. 5 is a graph showing correlations between a current density, and a power efficiency and an external quantum efficiency of the device prepared by compound CQ1; and FIG. 6 is an electroluminescence spectrum of example 7 at a current density of 20 $mA/cm^2$.

DETAILED DESCRIPTION OF EMBODIMENTS

The present disclosure will be further described below with reference to the accompanying drawings and specific embodiments, but the following examples are only preferred examples of the present disclosure, not all. All other examples obtained by those skilled in the art based on the examples of the embodiments without creative efforts shall fall within the protection scope of the present disclosure.

Example 1

An organic electronic material containing a nitrogen heterocycle was provided, the organic electronic material contained compound CQ1 and compound CQ1 had the following synthetic route:

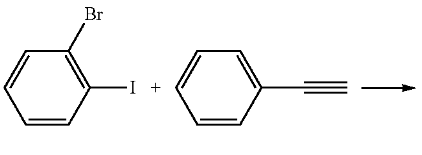

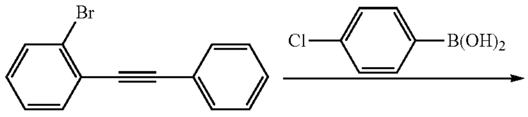

CQ1-1

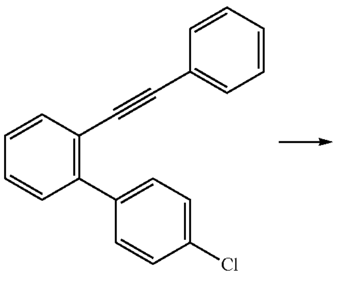

CQ1-2

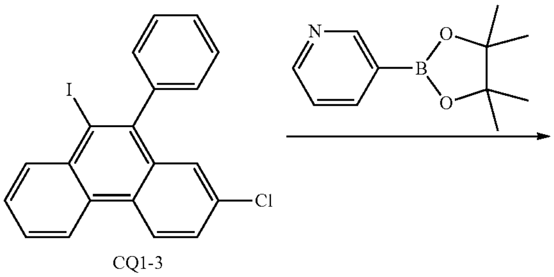

CQ1-3

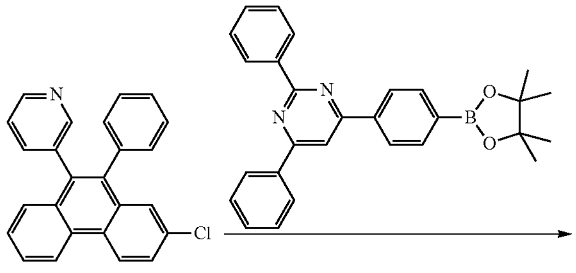

CQ1-4

-continued

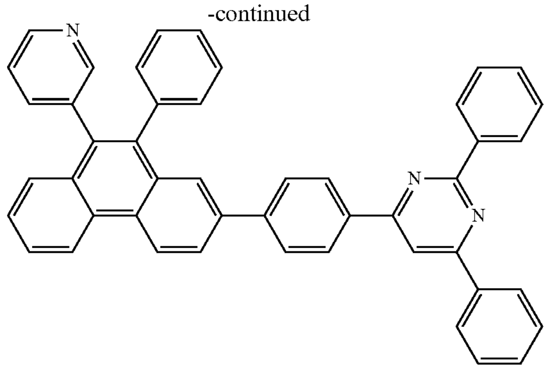

CQ1

Synthesis of Intermediate CQ1-1:

o-bromoiodobenzene (52.2 g, 184.5 mmol), phenylacetylene (18.85 g, 184.5 mmol) and triethylamine (260 mL) were added into a flask, cuprous iodide (0.35 g, 1.84 mmol) and triphenylphosphine palladium chloride (0.5 g, 0.7 mmol) were added under nitrogen protection, a reaction was carried out at a room temperature for 0.5 h while stirring was carried out, the reaction was stopped, an obtained product was filtered, the triethylamine was concentrated off, and 46.8 g of a yellow oily liquid with a yield of 98% was obtained.

$^1$H NMR (400 MHz, $CDCl_3$, δ): 7.62-7.64 (m, 2H), 7.57 (dd, J=7.2, 1.2 Hz, 1H), 7.51 (dd, J=5.2, 1.2 Hz, 1H), 7.32-7.40 (m, 5H).

Synthesis of Intermediate CQ1-2:

intermediate CQ1-1 (13.4 g, 52.1 mmol), p-chlorobenzeneboronic acid (8.5 g, 54.4 mmol) and potassium carbonate (14.4 g, 104.2 mmol) were added into the flask, toluene (80 mL), tetrahydrofuran (40 mL) and deionized water (40 mL) were added, triphenylphosphine palladium chloride (0.27 g, 0.38 mmol) was added under nitrogen protection, a reaction was carried out under reflux for 3 h, the reaction was stopped, cooling and liquid separation were carried out, and an organic phase was washed with water to be neutral and concentrated to obtain 16 g of a yellow oily liquid.

$^1$H NMR (400 MHz, $CDCl_3$, δ): 7.60-7.66 (m, 3H), 7.30-7.44 (m, 10H).

Synthesis of Intermediate CQ1-3:

intermediate CQ1-2 (15 g, 51.9 mmol) and dichloromethane (225 mL) were added into the flask, a temperature was reduced to 0-5° C., iodine chloride (10 g, 61.6 mmol) was dissolved in dichloromethane (75 mL) and dropwise added into the solution, after the dropwise adding, the solution was stirred for 0.5 h, 200 mL of a 5% sodium sulfite aqueous solution was dropwise added to quench a reaction until an obtained solution was neutral, liquid separation, drying, concentration and passing through a column were performed and thus 13 g of a light yellow solid with a yield of 60% was obtained.

$^1$H NMR (400 MHz, $CDCl_3$, δ): 8.61-8.67 (m, 2H), 8.45-8.48 (m, 1H), 7.68-7.75 (m, 2H), 7.53-7.62 (m, 4H), 7.37 (d, J=2.0 Hz, 1H), 7.26-7.29 (m, 2H).

Synthesis of Intermediate CQ1-4:

intermediate CQ1-3 (13.6 g, 32.8 mmol), 3-pyridylboronic acid pinacol ester (10 g, 48.8 mmol) and potassium carbonate (13.6 g, 98.4 mmol) were added into the flask, toluene (81 mL), ethanol (27 mL) and deionized water (27 mL) were added, triphenylphosphine palladium chloride (0.68 g, 0.97 mmol) was added under nitrogen protection, a reaction was carried out under reflux for 6 h, cooling and liquid separation were performed, an organic phase was washed with water, a part of a solvent was concentrated off, a solid was precipitated, an obtained solution was filtered, a filter cake was recrystallized once with toluene, and drying was performed and 9.7 g of a product with a yield of 81% was obtained.

$^1$H NMR (400 MHz, $CDCl_3$, δ): 8.73-8.77 (m, 2H), 8.42-8.46 (m, 2H), 7.63-7.73 (m, 2H), 7.45-7.56 (m, 4H), 7.09-7.29 (m, 6H).

Synthesis of Compound CQ1:

intermediate CQ1-4 (2 g, 5.5 mmol), 2,4-diphenyl-6-(4-phenylboronic acid pinacol)pyrimidine (2.5 g, 5.7 mmol) and potassium carbonate (2.3 g, 16.6 mmol) were added into the flask, toluene (20 mL), ethanol (10 mL) and deionized water (10 mL) were added, palladium acetate (0.06 g, 0.27 mmol) and x-phos (0.12 g, 0.54 mmol) were added under nitrogen, protection, a reaction was carried out under reflux for 2 h, a large amount of, a solid was precipitated, cooling and filtration were performed, a filter cake was washed with water to be neutral and washed with ethanol, and the filter cake was dried. The filter cake was recrystallized once with toluene and dried to obtain 2.5 g of a product with a yield of 71%.

$^1$H NMR (400 MHz, $CDCl_3$, δ): 8.86 (d, 1H), 8.64-8.73 (m, 3H), 8.34-8.36 (m, 2H), 8.05-8.15 (m, 5H), 7.95-7.98 (m, 1H), 7.89-7.92 (m, 2H), 7.78-7.81 (m, 2H), 7.64-7.67 (m, 2H), 7.36-7.60 (m, 14H). MS (ESI, m/z): $[M+H]^+$: 638.74.

Example 2

An organic electronic material containing a nitrogen heterocycle was provided, the organic electronic material contained compound CQ2 and compound CQ2 had the following synthetic route:

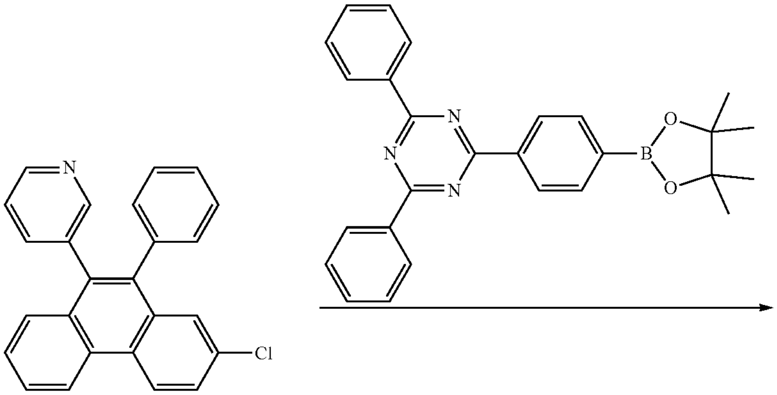

CQ1-4

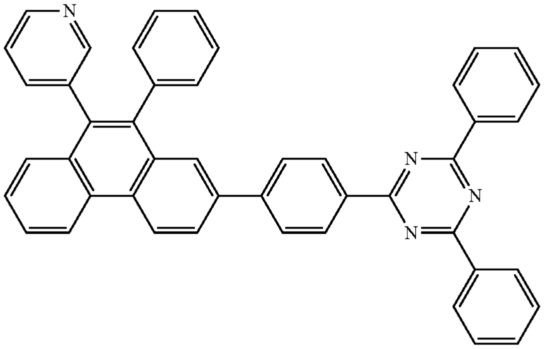

CQ2

Figure 1:
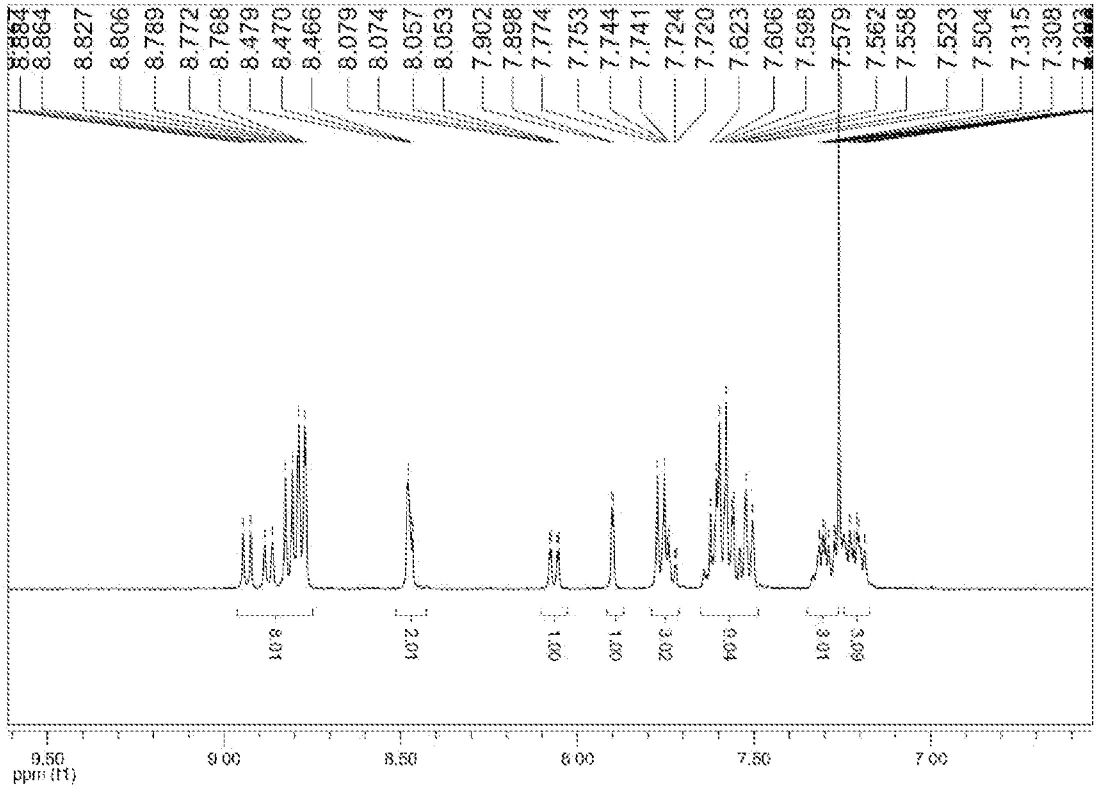
FIG. 1 is a proton nuclear magnetic resonance spectrum of compound CQ2.

Synthesis of Compound CQ2 intermediate CQ1-4 (2 g, 5.5 mmol), 2,4-diphenyl-6-(4-phenylboronic acid pinacol)-1,3,5-triazine (2.5 g, 5.7 mmol) and potassium carbonate (2.3 g, 16.6 mmol) were added into the flask, toluene (20 mL), ethanol (10 mL) and deionized water (10 mL) were added, palladium acetate (0.06 g, 0.27 mmol) and x-phos (0.12 g, 0.54 mmol) were added under nitrogen protection, a reaction was carried out under reflux for 2 h, a large amount of a solid was precipitated, cooling and filtration were performed, a filter cake was washed with water to be neutral and washed with ethanol, and the filter cake was dried. The filter cake was recrystallized once with toluene and dried to obtain 2.2 g of a product with a yield of 63%. The obtained product was compound CQ2 whose proton nuclear magnetic resonance spectrum was shown in FIG. 1.

$^1$H NMR: (400 MHz, $CDCl_3$) δ 8.77-8.95 (m, 8H), 8.47-8.48 (m, 2H), 8.05-8.08 (m, 1H), 7.90 (d, 1H), 7.72-7.77 (m, 3H), 7.50-7.62 (m, 9H), 7.27-7.32 (m, 3H), 7.19-7.23 (m, 3H). MS (ESI, m/z): $[M+H]^+$: 639.52.

Example 3

An organic electronic material containing a nitrogen heterocycle was provided, the organic electronic material contained compound CQ5 and compound CQ5 had the following synthetic route:

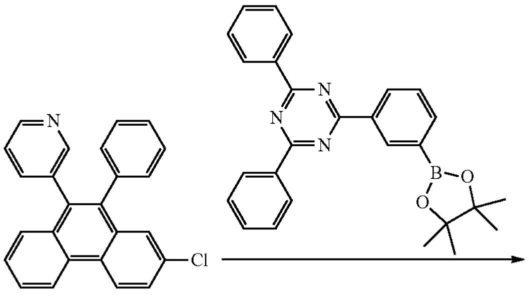

CQ1-4

-continued

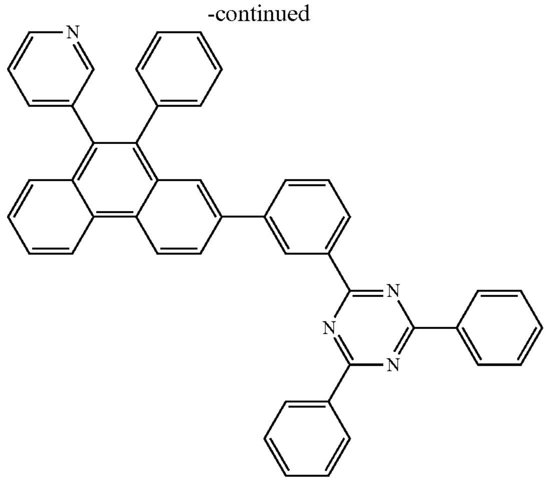

CQ5

Synthesis of Compound CQ5 intermediate CQ1-4 (8 g, 21.9 mmol), 2,4-diphenyl-6-(3-phenylboronic acid pinacol)-1,3,5-triazine (10 g, 23.0 mmol) and potassium carbonate (9.1 g, 65.8 mmol) were added into the flask, toluene (80 mL), ethanol (40 mL) and deionized water (40 mL) were added, palladium acetate (0.24 g, 1.1 mmol) and x-phos (0.48 g, 2.2 mmol) were added under nitrogen protection, a reaction was carried out under reflux for 2 h, a large amount of a solid was precipitated, cooling and filtration were performed, a filter cake was washed with water to be neutral and washed with ethanol, and the filter cake was dried. The filter cake was recrystallized once with toluene and dried to obtain 4.6 g of a product with a yield of 33%.

$^1$H NMR (400 MHz, $CDCl_3$, δ): 8.88-8.98 (m, 3H), 8.74-8.78 (m, 5H), 8.47-8.49 (m, 2H), 8.10-8.13 (m, 1H), 7.94 (s, 1H), 7.73-7.81 (m, 2H), 7.51-7.64 (m, 10H), 7.21-7.30 (m, 6H). MS (ESI, m/z): $[M+H]^+$: 639.34.

Example 4

An organic electronic material containing a nitrogen heterocycle was provided, the organic electronic material contained compound CQ7 and compound CQ7 had the following synthetic route:

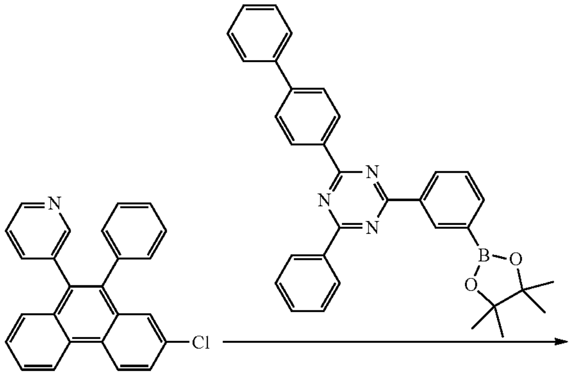

CQ1-4

-continued

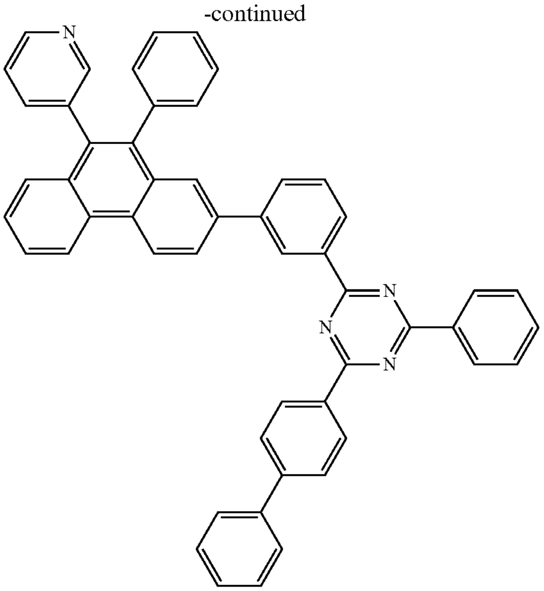

CQ7

Synthesis of Compound CQ7 intermediate CQ1-4 (2 g, 5.5 mmol), 2-phenyl-4-biphenyl-6-(3-phenylboronic acid pinacol)-1,3,5-triazine (2.9 g, 5.7 mmol) and potassium carbonate (2.3 g, 16.6 mmol) were added into the flask, toluene (20 mL), ethanol (10 mL) and deionized water (10 mL) were added, palladium acetate (0.06 g, 0.27 mmol) and x-phos (0.12 g, 0.54 mmol) were added under nitrogen protection, a reaction was carried out under reflux for 3 h, a large amount of a solid was precipitated, cooling and filtration were performed, a filter cake was washed with water to be neutral and washed with ethanol, and the filter cake was dried. The filter cake was recrystallized once with toluene and dried to obtain 2.9 g of a product with a yield of 74%.

$^1$H NMR (400 MHz, $CDCl_3$, δ): 8.92 (d, J=2.0 Hz, 1H), 8.86 (d, 1H), 8.68-8.73 (m, 2H), 8.64-8.66 (m, 1H), 8.39-8.43 (m, 2H), 8.12-8.14 (m, 1H), 8.06-8.09 (m, 1H), 7.99-8.05 (m, 2H), 7.95-7.98 (m, 2H), 7.89-7.92 (m, 1H), 7.64-7.72 (m, 3H), 7.42-7.61 (m, 15H), 7.35-7.40 (m, 2H), MS (ESI, m/z): $[M+H]^+$: 715.48.

Example 5

An organic electronic material containing a nitrogen heterocycle was provided, the organic electronic material contained compound CQ10 and compound CQ10 had the following synthetic route:

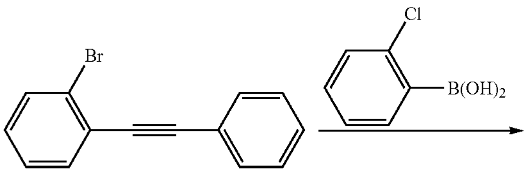

CQ1-1

-continued

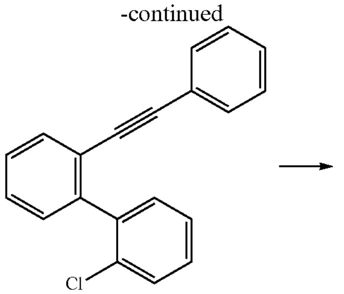

CQ10-1

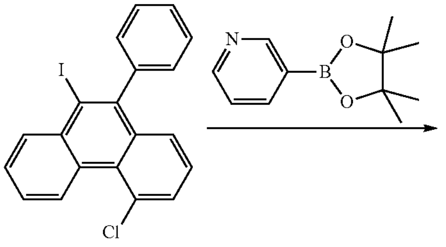

CQ10-2

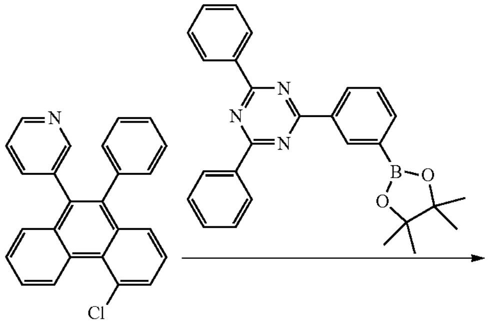

CQ10-3

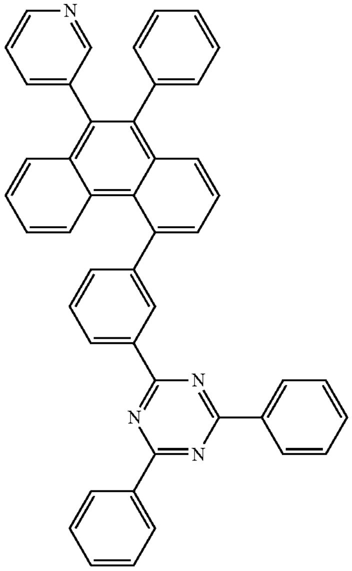

CQ10

Synthesis of Intermediate CQ10-1:

intermediate CQ1-1 (15 g, 58.3 mmol), o-chlorophenylboronic acid (10 g, 63.9 mmol) and potassium carbonate (20 g, 144.7 mmol) were added into the flask, toluene (90 mL), tetrahydrofuran (45 mL) and deionized water (45 mL) were added, triphenylphosphine palladium chloride (0.3 g, 0.43 mmol) was added under nitrogen protection, a reaction was carried out under reflux for 4 h, the reaction was stopped, cooling and liquid separation were carried out, and an organic phase was washed with water to be neutral and concentrated to obtain 11.5 g of a yellow oily liquid with a yield of 68%.

$^1$H NMR (400 MHz, $CDCl_3$, δ): 7.67-7.70 (m, 1H), 7.61-7.64 (m, 2H), 7.51-7.56 (m, 3H), 7.45-7.49 (m, 1H), 7.38-7.44 (m, 3H), 7.34-7.37 (m, 3H).

Synthesis of Intermediate CQ10-2:

intermediate CQ1-1 (9.5 g, 32.9 mmol) and dichloromethane (150 mL) were added into the flask, a temperature was reduced to 0-5° C., iodine chloride (6.4 g, 39.4 mmol) was dissolved in dichloromethane (50 mL) and dropwise added into the solution, after the dropwise adding, the solution was stirred for 0.5 h, 150 mL of a 5% sodium sulfite aqueous solution was dropwise added to quench a reaction until an obtained solution was neutral, liquid separation, drying, concentration and passing through a column with petroleum ether were performed and thus 13.9 g of a light yellow oily liquid was obtained.

$^1$H NMR (400 MHz, $CDCl_3$, δ): 9.77-9.80 (m, 1H), 8.52-8.54 (m, 1H), 7.71-7.74 (m, 3H), 7.54-7.56 (m, 3H), 7.35-7.36 (m, 1H), 7.25-7.30 (m, 3H).

Synthesis of Intermediate CQ10-3:

intermediate CQ10-2 (12 g, 28.9 mmol), 3-pyridylboronic acid pinacol ester (8.9 g, 43.4 mmol) and potassium carbonate (12 g, 86.8 mmol) were added into the flask, toluene (120 mL), ethanol (60 mL) and deionized water (60 mL) were added, triphenylphosphine palladium chloride (0.6 g, 0.85 mmol) was added under nitrogen protection, a reaction was carried out under reflux for 6 h, cooling and liquid separation were performed, an organic phase was washed with water, a part of a solvent was concentrated off, a solid was precipitated, an obtained solution was filtered, a filter cake was recrystallized once with toluene, and drying was performed and 7.9 g of a product with a yield of 75% was obtained.

$^1$H NMR (400 MHz, $CDCl_3$, δ): 9.76 (d, 1H), 8.41-8.46 (m, 2H), 7.66-7.79 (m, 2H), 7.43-7.57 (m, 4H), 7.34-7.38 (m, 1H), 7.07-7.29 (m, 6H).

Synthesis of Compound CQ10:

intermediate CQ1-4 (2 g, 5.5 mmol), 2,4-diphenyl-6-(3-phenylboronic acid pinacol)-1,3,5-triazine (2.5 g, 5.7 mmol) and potassium carbonate (2.3 g, 16.6 mmol) were added into the flask, toluene (20 mL), ethanol (10 mL) and deionized water (10 mL) were added, palladium acetate (0.06 g, 0.27 mmol) and x-phos (0.12 g, 0.54 mmol) were added under nitrogen protection, a reaction was carried out under reflux for 2 h, cooling and filtration were performed, a filter cake was washed with water to be neutral and washed with ethanol, and the filter cake was dried. The filter cake was recrystallized once with toluene and dried to obtain 2.8 g of a product with a yield of 80%.

$^1$H NMR (400 MHz, $CDCl_3$, δ): 9.00-9.01 (d, 1H), 8.88-8.89 (m, 1H), 8.76-8.79 (m, 4H), 8.45-8.49 (m, 2H), 8.02-8.04 (m, 1H), 7.42-7.68 (m, 13H), 7.01-7.33 (m, 8H). MS (ESI, m/z): $[M+H]^+$: 639.39.

Example 6

An organic electronic material containing a nitrogen heterocycle was provided, the organic electronic material contained compound CQ21 and compound CQ21 had the following synthetic route:

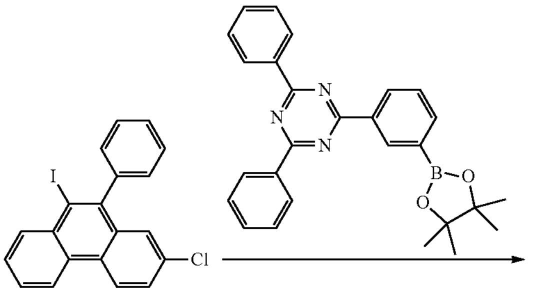

CQ1-3

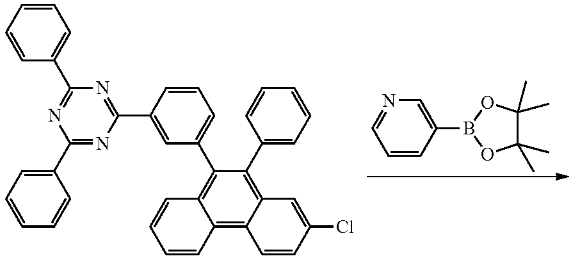

CQ21-1

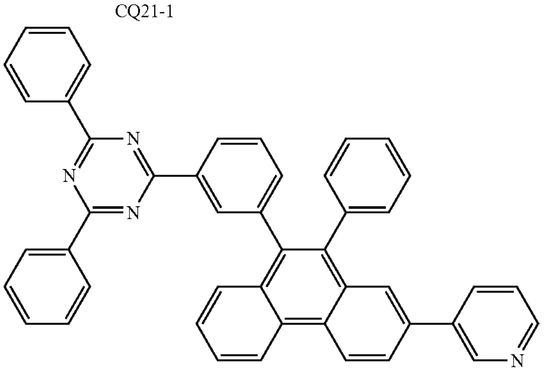

CQ21

Synthesis of Intermediate CQ21-1:

intermediate CQ1-3 (6 g, 14.5 mmol), 2,4-diphenyl-6-(3-phenylboronic acid pinacol)-1,3,5-triazine (6.6 g, 15.2 mmol) and potassium carbonate (6 g, 43.4 mmol) were added into the flask, toluene (36 mL), ethanol (18 mL) and deionized water (18 mL) were added, triphenylphosphine palladium chloride (0.18 g, 0.28 mmol) was added under nitrogen protection, a reaction was carried out under reflux for 3 h, cooling and liquid separation were performed, an organic phase was washed with water, a part of a solvent was concentrated off, a solid was precipitated, an obtained solution was filtered, a filter cake was recrystallized once with toluene, and drying was performed and 7.6 g of a product with a yield of 88% was obtained.

$^1$H NMR (400 MHz, $CDCl_3$, δ): 8.60-8.81 (m, 8H), 7.39-7.74 (m, 13H), 7.27-7.29 (m, 2H), 7.16-7.22 (m, 3H).

Figure 2:
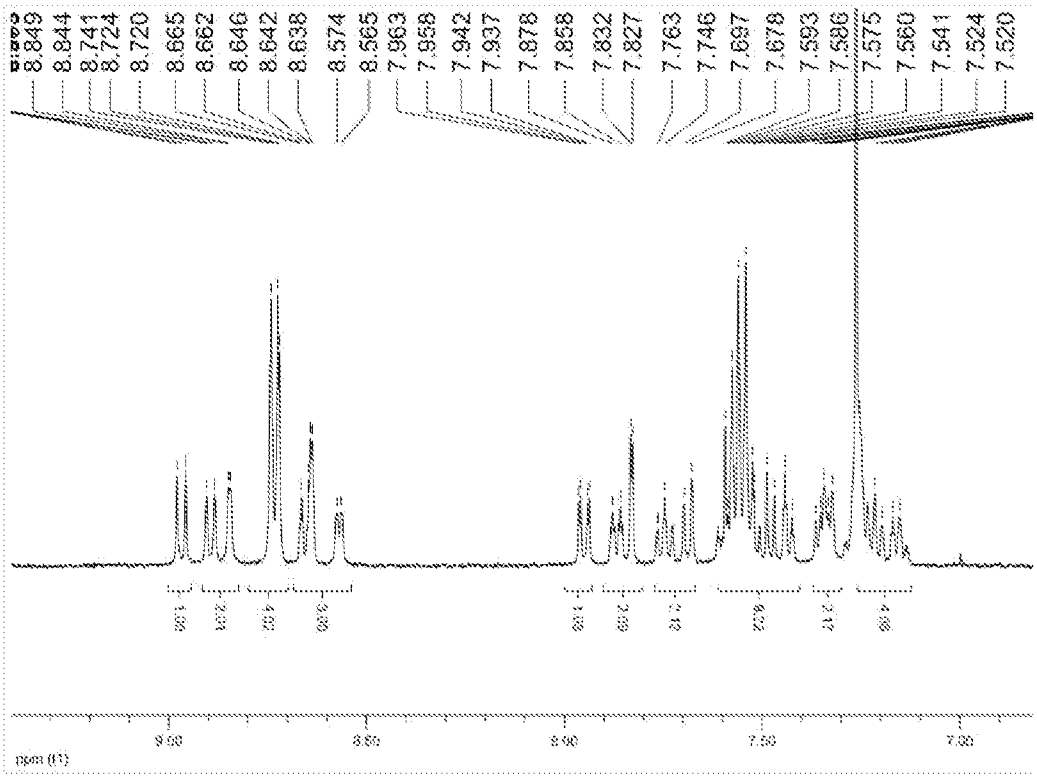
FIG. 2 is a proton nuclear magnetic resonance spectrum of compound CQ21.

Synthesis of Intermediate CQ21:

intermediate CQ21-1 (4.7 g, 7.9 mmol), 3-pyridylboronic acid pinacol ester (2.5 g, 5.7 mmol) and potassium carbonate (3.3 g, 23.9 mmol) were added into the flask, toluene (30 mL), dioxane (30 mL) and deionized water (15 mL) were added, palladium acetate (0.14 g, 0.63 mmol) and x-phos (0.28 g, 1.3 mmol) were added under nitrogen protection, a reaction was carried out under reflux for 5 h, cooling and filtration were performed, a filter cake was washed with water to be neutral and washed with ethanol, and the filter cake was dried. The filter cake was recrystallized once with toluene and dried to obtain 4.2 g of a product with a yield of 84%. The obtained product was compound CQ21 whose proton nuclear magnetic resonance spectrum was shown in FIG. 2.

$^1$H NMR (400 MHz, $CDCl_3$, δ): 8.96-8.98 (d, 1H), 8.84-8.91 (m, 2H), 8.72-8.74 (m, 4H), 8.57-8.67 (m, 3H), 7.94-7.96 (m, 1H), 7.83-7.88 (m, 2H), 7.68-7.76 (m, 2H), 7.42-7.59 (m, 9H), 7.32-7.36 (m, 2H), 7.15-7.22 (m, 4H). MS (ESI, m/z): $[M+H]^+$: 639.28.

Effects of the compounds of the present disclosure will be described in detail below with reference to examples.

Figure 3:
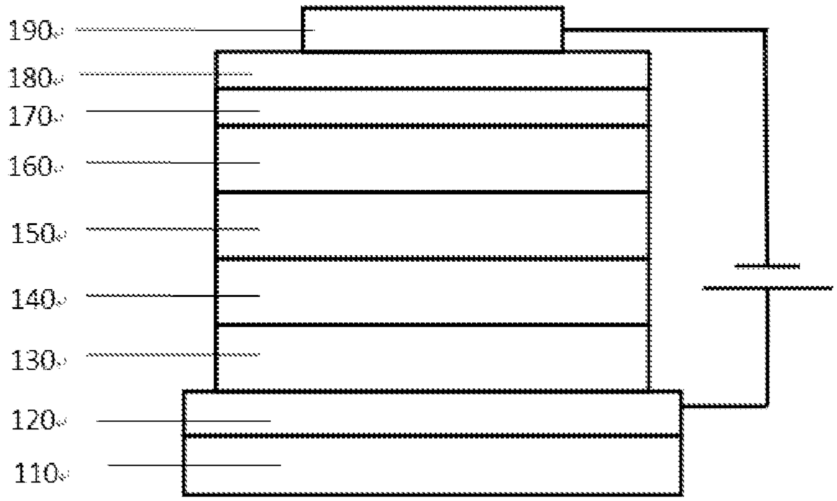
FIG. 3 is a structural diagram of an organic light-emitting device of the present disclosure.

Preparation of an organic light-emitting device whose structural diagram was shown in FIG. 3. A specific device structure was as follows: glass/anode (ITO)/hole injection layer (HIL)/hole transport layer (HTL)/electron blocking layer (EBL)/light-emitting layer (host material GH:green light emitting material GD)/electron transport layer (ETL)/electron, injection layer (LiF)/cathode (Al).

Example 7

Preparation of OLED Using Compound CQ1 of Example 1

(1) A transparent and, conductive ITO glass substrate 110 (with an anode 120 on top) (CSG Holding Co., Ltd.) was subjected to ultrasonic treatment in a commercial detergent, rinsed in deionized water, sequentially washed with ethanol, acetone and deionized water, baked in a clean environment to completely remove water, washed with ultraviolet photosynthetic ozone, and treated with oxygen plasma for 30 s.

(2) The glass substrate with the anode was placed in a vacuum chamber, vacuum pumping was carried out, and HIL (60 nm) was evaporated on the ITO to be used as a hole injection layer 130 at a rate of 0.1 nm/s.

(3) A compound NPB was evaporated on the hole injection layer to form a hole transport layer 140 having a thickness of 10 nm at a rate of 0.1 nm/s, TCTA was evaporated to form an electron blocking layer 150 having a thickness of 5 nm at a rate of 0.1 nm/s.

(4) A light-emitting layer 160 having a thickness of 20 nm was evaporated on the hole blocking layer at a rate of 0.1 nm/s, where CBP was a host light-emitting material, Ir(ppy)3 in an amount of 5 wt % was a phosphorescent dopant guest material.

(5) Compound CQ1 was evaporated on a light-emitting layer to a thickness of 30 nm, as an electron transport layer 170 at a rate of 0.1 nm/s, 1 nm LiF was evaporated to form an electron injection layer 180, and 80 nm Al was used as a cathode 190 of the device.

Example 8

An only difference from example 7 was that in step (5), compound CQ2 having a thickness of 30 nm was evaporated on a light-emitting layer as an electron transport layer 170.

Example 9

An only difference from example 7 was that in step (5), compound CQ5 having a thickness of 30 nm was evaporated on a light-emitting layer as, an electron transport layer 170.

Example 10

An only difference from example 7 was that in step (5), compound CQ7 having a thickness of 30 nm was evaporated on a light-emitting layer as an electron transport layer 170.

Example 11

An only difference from example 7 was that in step (5), compound CQ10 having a thickness of 30 nm was evaporated on a light-emitting layer as an electron transport layer 170.

Example 12

An only difference from example 7 was that in step (5), compound CQ21 having a thickness of 30 nm was evaporated on a light-emitting layer as an electron transport layer 170.

Comparative Example 1

An only difference from example 7 was that compound 8 (i.e.: ET1) described in manufacturing example 8 disclosed in Chinese Patent CN107445910A was used instead of compound CQ1 used in step (5).

Comparative Example 2

An only difference from example 7 was that compound 37 (i.e.: ET2) described in example 5 disclosed in Chinese Patent CN108299388A was used instead of compound CQ1 used in step (5).

Comparative Example 3

An only difference from example 7 was that compound Alq3 was used instead of compound CQ1 used in step (5).

Experimental Example 1

The prepared devices were measured using a Photo Research PR650 spectrometer for operating voltage, brightness, efficiency, and CIE coordinates at a current density of 20 mA/cm$^2$ and time (T90) for the brightness to become 90% of the initial brightness at this current density.

The results were specifically shown in Table 1. FIG. 4 is a graph showing a correlation between a current density and a current efficiency of the device; FIG. 5 is a graph showing correlations between a current density, and a power efficiency and an external quantum efficiency of the device prepared by compound CQ1; and FIG. 6 is an electroluminescence spectrum of the device prepared by compound CQ1 at a current density of 20 mA/cm$^2$.

TABLE 1

| Example | Compound | Voltage (V) | Brightness (cd/m$^2$) | Power efficiency (lm/W) | Current efficiency (cd/A) | External quantum efficiency | CIE (x, y) | T90 (h) |
|---|---|---|---|---|---|---|---|---|
| 7 | CQ1 | 6.90 | 10028 | 22.9 | 50 | 14.7% | (0.2587, 0.6328) | 146 |
| 8 | CQ2 | 6.52 | 10804 | 26.2 | 54 | 16.0% | (0.2584, 0.6395) | 175 |
| 9 | CQ5 | 6.76 | 11208 | 25.7 | 56 | 16.3% | (0.2596, 0.6374) | 168 |
| 10 | CQ7 | 6.84 | 10204 | 23.6 | 52 | 14.9% | (0.2581, 0.6348) | 153 |
| 11 | CQ10 | 6.67 | 10956 | 25.8 | 55 | 16.7% | (0.2542, 0.6328) | 165 |
| 12 | CQ21 | 6.94 | 11649 | 23.4 | 57 | 16.1% | (0.2553, 0.6318) | 157 |
| Comparative example 1 | ET1 | 7.43 | 7762 | 17.8 | 43 | 12.5% | (0.2586, 0.6381) | 98 |
| Comparative example 2 | ET2 | 7.28 | 8678 | 19.1 | 44 | 12.9% | (0.2597, 0.6313) | 109 |
| Comparative example 3 | Alq3 | 7.61 | 6327 | 14.1 | 32 | 9.4% | (0.2583, 0.6327) | 76 |

As can be seen from experimental data of Table 1, FIG. 4 and FIG. 5, the organic electronic material containing a nitrogen heterocycle of the present disclosure represented by chemical formula I or II can be used in an organic light-emitting device as an electron transport material.

The organic light-emitting devices prepared from the organic electronic material containing a nitrogen heterocycle had a lower working voltage than that of comparative examples 1-3 in the prior art, a high brightness, and an improved current efficiency, power efficiency and external quantum efficiency under a same current density. Meanwhile, under the same current density, the devices prepared from the compounds of the present disclosure had a greatly prolonged service life compared with the comparative examples in the prior art. Under the same current density, the organic electronic material of the present disclosure had a better electron transport capability, thus the devices had a lower working voltage, a less power consumption and an improved service life.

The excellent performances were mainly gained by simultaneously introducing pyridine and pyrimidine or triazine into different positions of phenanthryl to obtain the organic electronic material containing a nitrogen heterocycle which can effectively reduce an HOMO energy level and an LUMO energy level, increase an electron injection and transmission capacity, reduce the working voltage of the devices and improve the efficiency. Meanwhile, asymmetric groups were introduced into different positions of phenanthrene, such that a mutual influence of different groups can be reduced, the thermal stability of the material can be improved, an amorphous film can be prepared, the efficiency of the devices was improved, and the service, life of the devices was prolonged.

The structural formulas in the device were as follows:

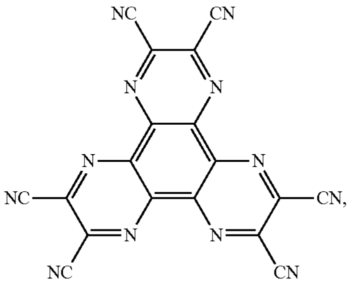

HIL

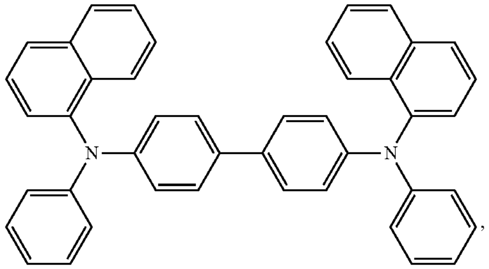

NPB

-continued

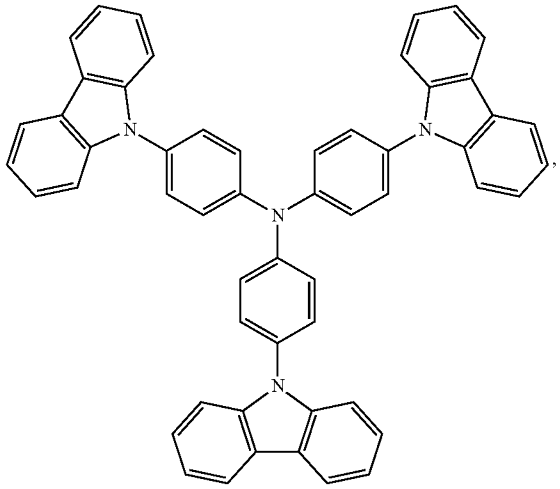

TCTA

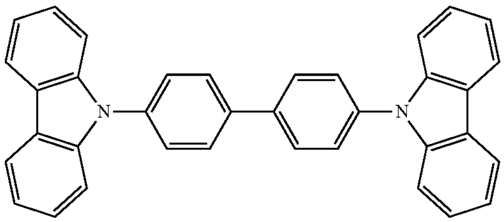

CBP

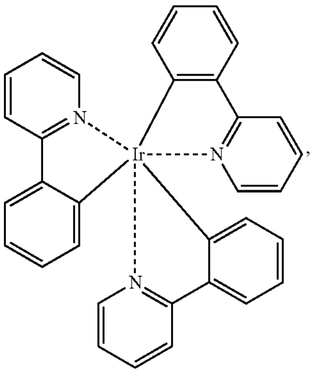

Ir(ppy)3

ET1

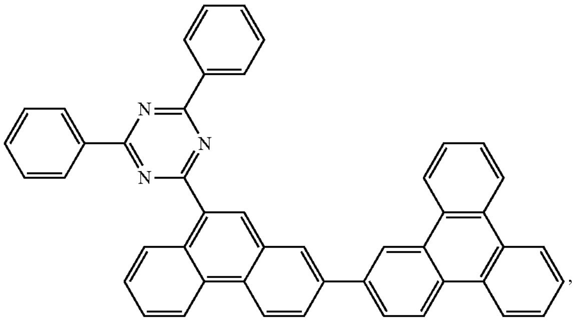

-continued

ET2

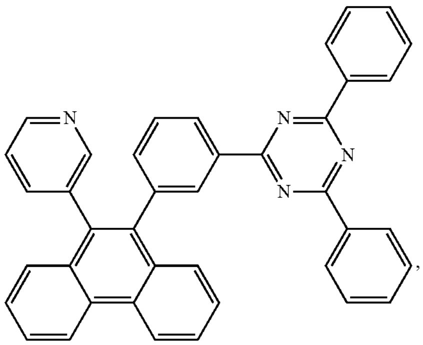

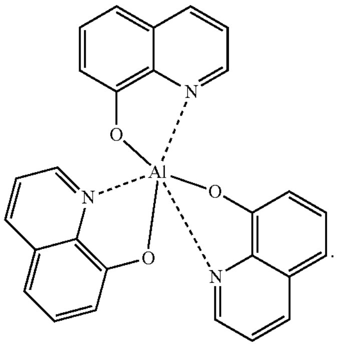

Alq3

The above organic materials are all existing known materials and commercially available.

The foregoing is detailed description of the preferred specific examples of the present disclose. It should be understood that, a person of ordinary skill in the art can make various modifications and variations according to the concept of the present disclosure without creative efforts. Therefore, all technical solutions that, can be obtained by those skilled in the art based on the prior art through logical analysis, reasoning, or finite experiments according to the concept of the present disclosure shall fall within the protection scope defined by the appended claims.

The invention claimed is:

1. An organic electronic material containing a nitrogen heterocycle, wherein the organic electronic material contains a compound of the following structural formula (I) or (II):

formula (I)

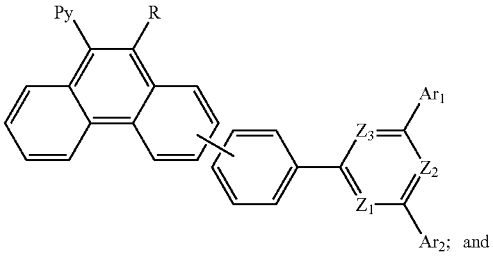

and

-continued formula (II)

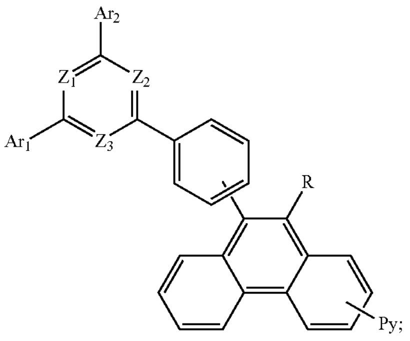

and wherein Py is substituted or unsubstituted $C_5$-$C_{30}$ pyridine;

R is hydrogen, $C_1$-$C_4$ alkyl, and substituted or unsubstituted $C_6$-$C_{30}$ aryl;

$Ar_1$ and $Ar_2$ are independently selected from substituted or unsubstituted $C_6$-$C_{30}$ aryl; and at least one of $Z_1$, $Z_2$ and $Z_3$ is N and the others are CH.

2. The organic electronic material according to claim 1, wherein R is independently selected from the group consisting of hydrogen, phenyl, tolyl, biphenyl, or naphthyl; and $Ar_1$ and $Ar_2$ are independently selected from the group consisting of phenyl, tolyl, biphenyl, naphthyl, phenanthryl, anthracyl, perylenyl, phenylnaphthyl, naphthylphenyl, diphenylphenyl, 9,9-dimethylfluorenyl, 9,9-diphenylfluorenyl, 9,9-spirobifluorenyl, dibenzofuranyl, dibenzothienyl, or benzophenanthryl.

3. The organic electronic material according to claim 1, wherein Py is pyridyl, R is phenyl, and $Ar_1$ and $Ar_2$ are independently selected from the group consisting of phenyl, biphenyl or naphthyl.

4. The organic electronic material according to claim 1, wherein the organic electronic material contains any one of the following compounds CQ1-CQ28:

CQ 1

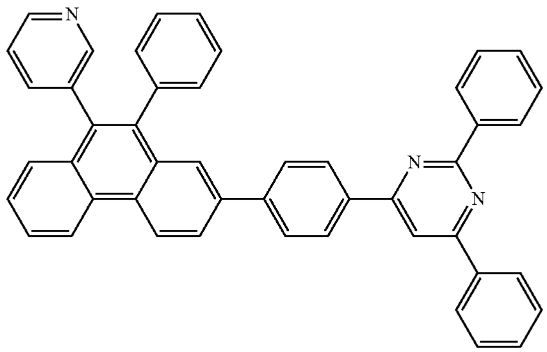

-continued
CQ 2
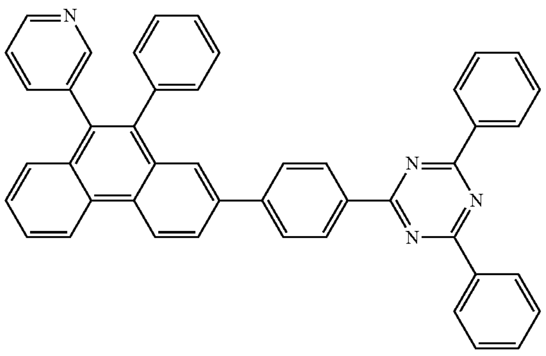
CQ 3
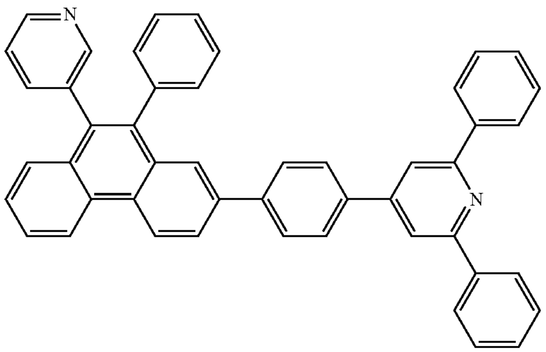
CQ 4
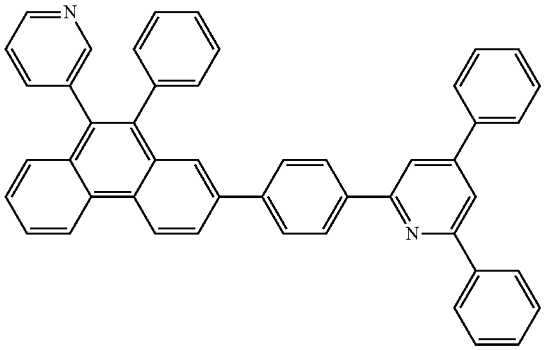
CQ 5
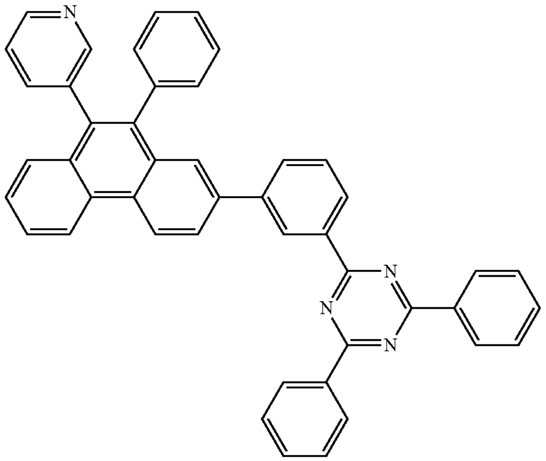
-continued
CQ 6
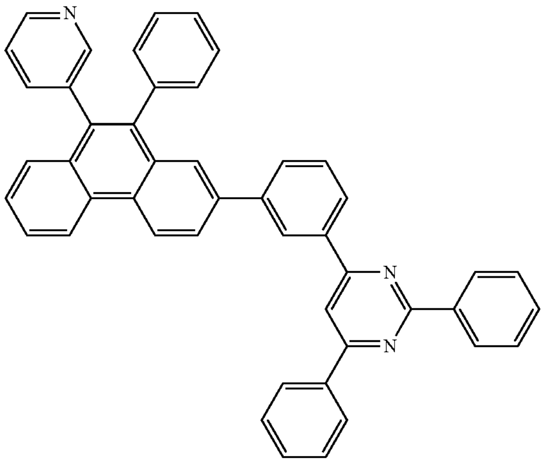
CQ 7
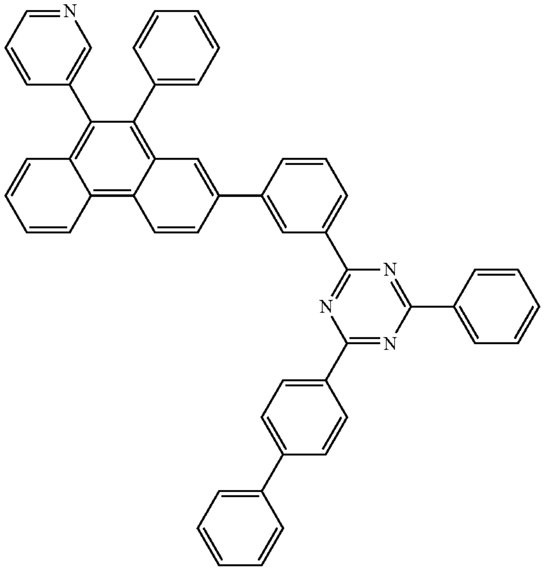
CQ 8
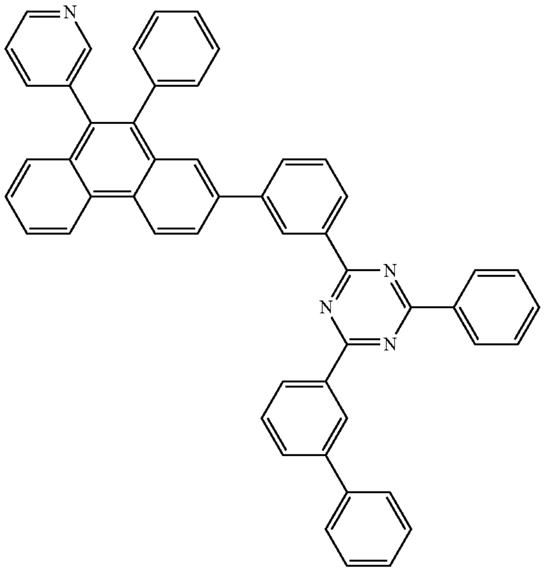

-continued
CQ 9
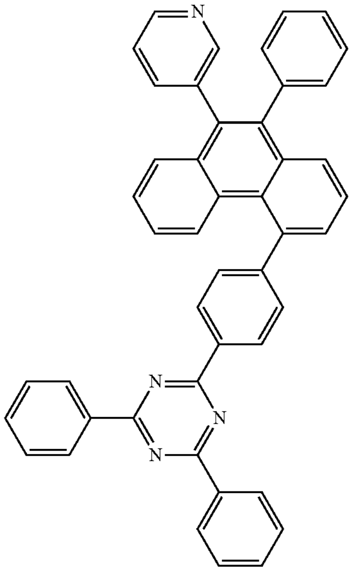
CQ 10
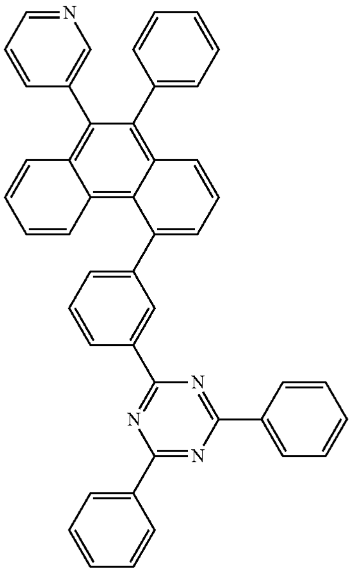
-continued
CQ 11
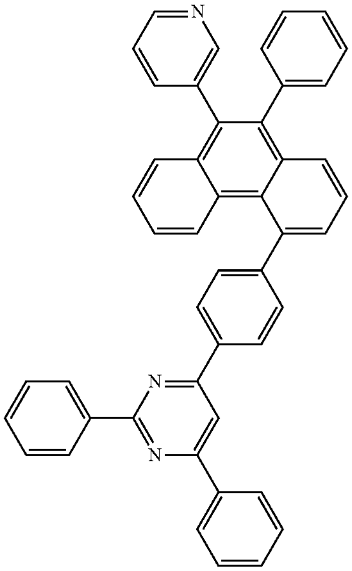
CQ 12
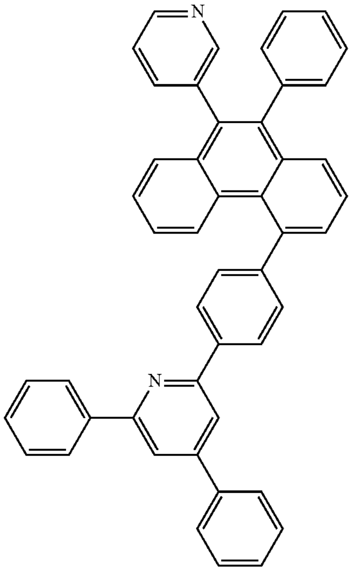
CQ 13
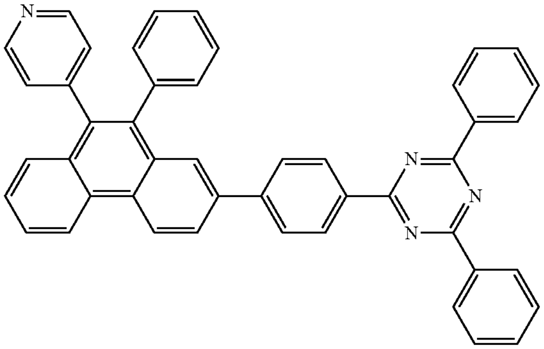

-continued
CQ 14
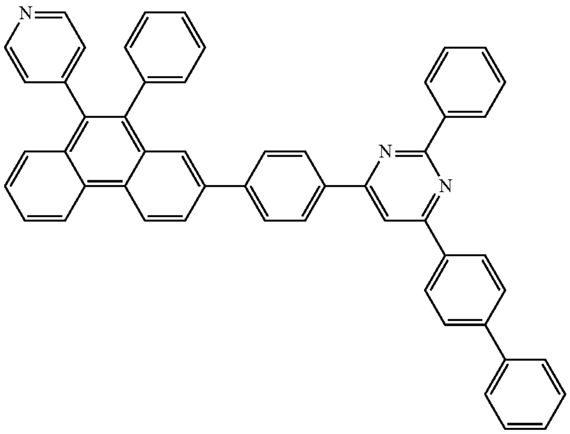
CQ 15
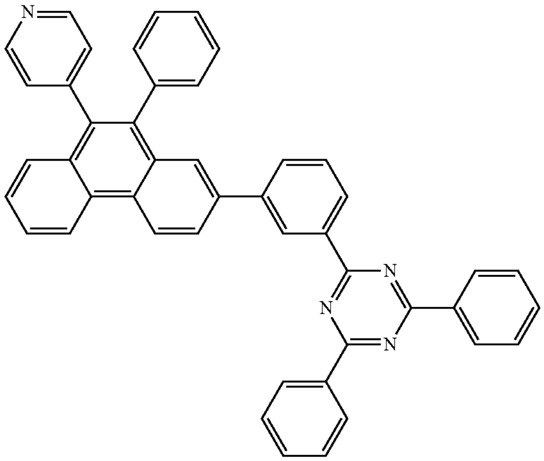
CQ 16
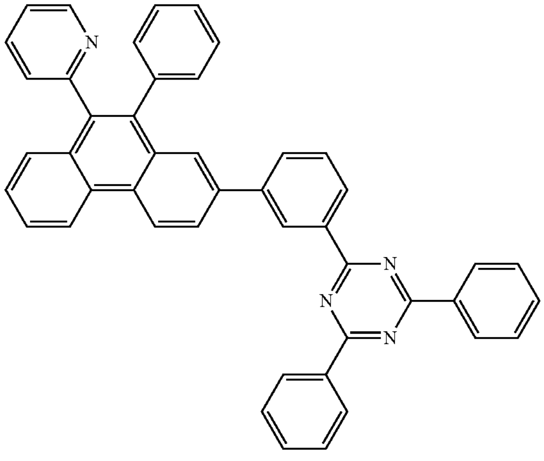
-continued
CQ 17
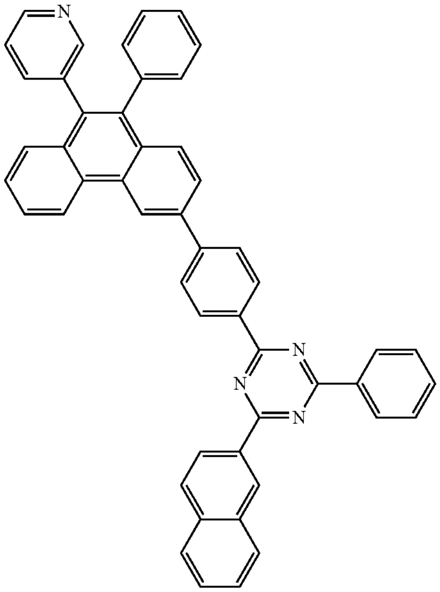
CQ 18
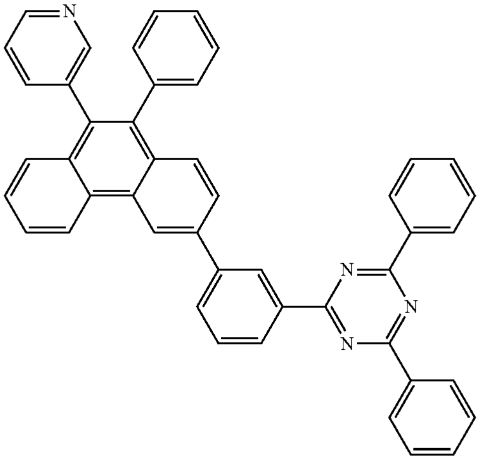
CQ 19
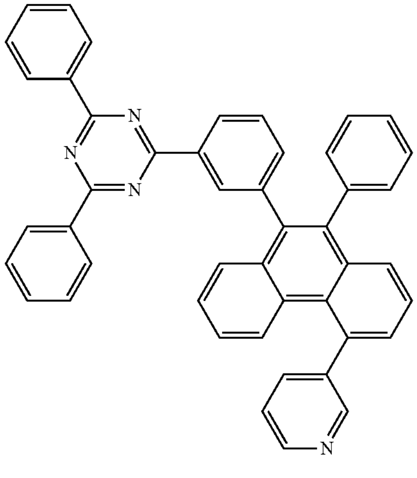

-continued
CQ 20
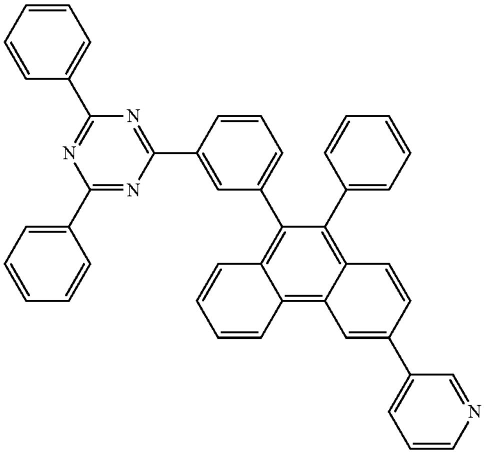
CQ 21
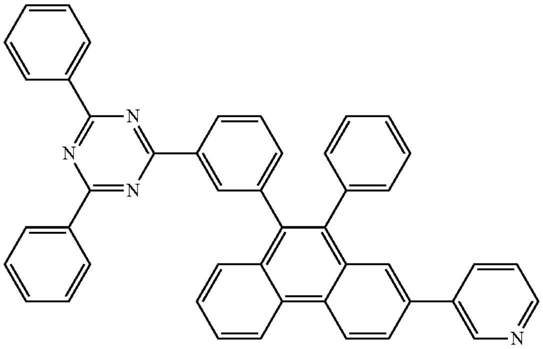
CQ 22
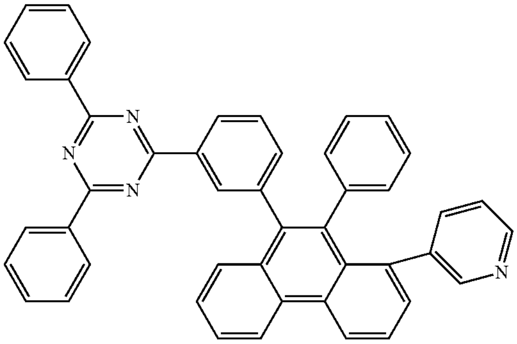
-continued
CQ 23
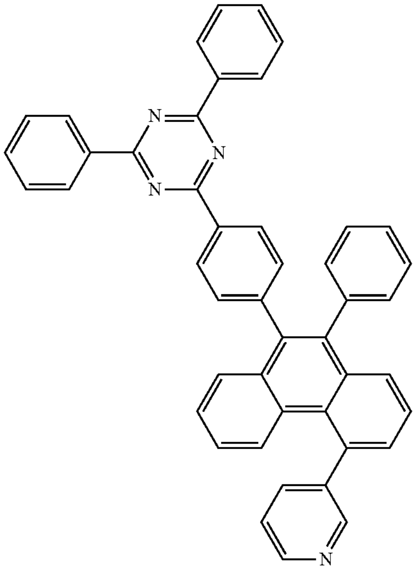
CQ 24
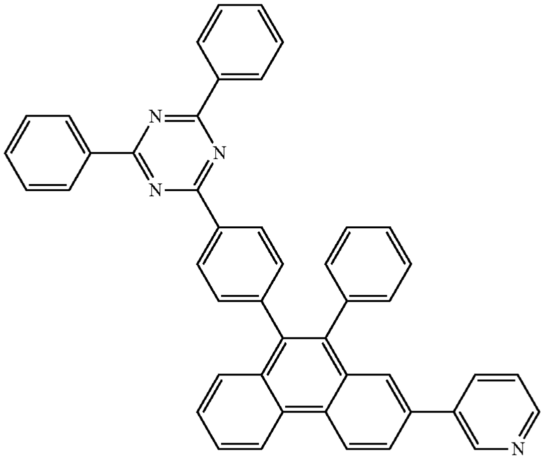
CQ 25
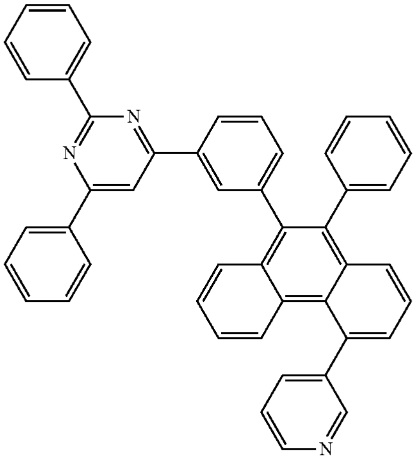

-continued

CQ 26

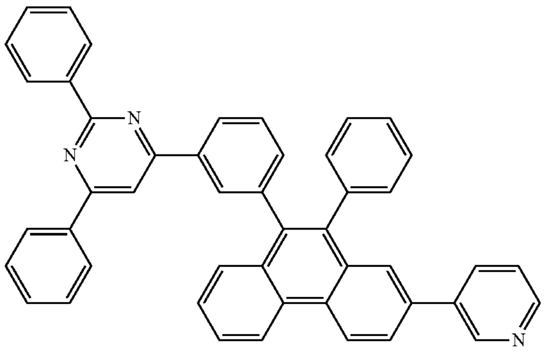

CQ 27

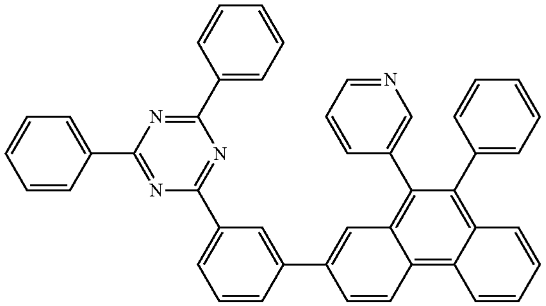

CQ 28

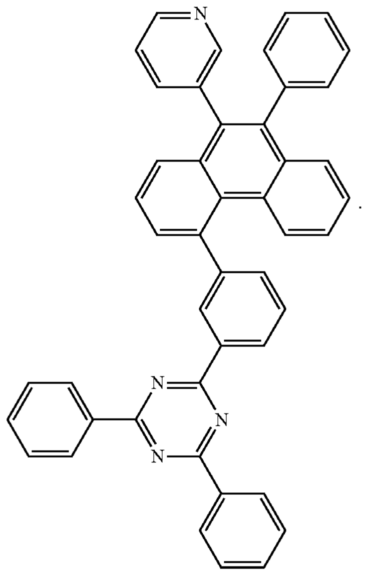

5. The organic electronic material according to claim 1, wherein a method for preparing the compound of structural formula (I) or (II) comprises the following steps:

(A1) synthesis of compound b: preparing compound b by a Sonogashira reaction of o-bromoiodobenzene with an alkynyl compound;

(A2) synthesis of compound c: preparing compound c by a Suzuki reaction of compound b with halogenated phenylboronic acid;

(A3) synthesis of compound d: preparing compound d by reacting compound c with iodine chloride or bromosuccinimide, wherein a solvent is dichloromethane, chloroform, tetrahydrofuran, 1,2-dichloroethane, acetonitrile, N,N-dimethylformamide, N,N-dimethylacetamide or dioxane;

(A4) synthesis of compound f: obtaining compound f by a Suzuki reaction of compound d and pyridinylboronic acid e or a pyridinylboronic ester; and (A5) synthesis of compound of structural formula (I): obtaining compound of structural formula (I) by a Suzuki reaction of compound f with boronate ester h;

or (B1) synthesis of compound b: preparing compound b by a Sonogashira reaction of o-bromoiodobenzene with an alkynyl compound;

(B2) synthesis of compound c: preparing compound c by a Suzuki reaction of compound b with halogenated phenylboronic acid;

(B3) synthesis of compound d: in a reaction of step 3, preparing compound d by reacting compound c with iodine chloride or bromosuccinimide, wherein a solvent is dichloromethane, chloroform, tetrahydrofuran, 1,2-dichloroethane, acetonitrile, N,N-dimethylformamide, N,N-dimethylacetamide or dioxane;

(B4) synthesis of compound j: obtaining compound j by a Suzuki reaction of compound d and boronate ester h; and (B5) synthesis of compound of structural formula (II): obtaining compound of structural formula (II) by a Suzuki reaction of compound j with pyridinylboronic acid e or a pyridinylboronic ester;

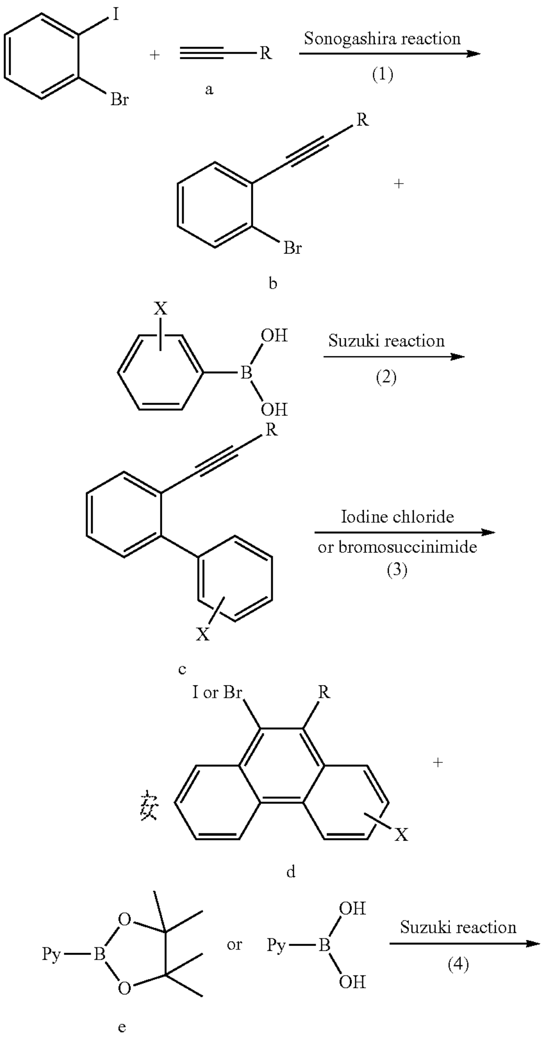

-continued

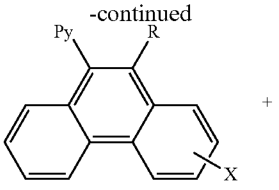

f

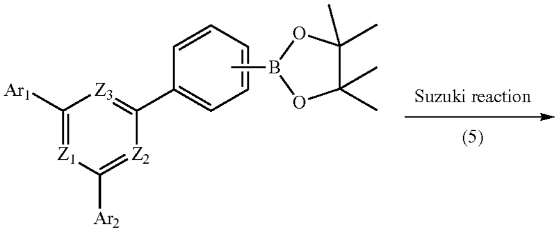

h

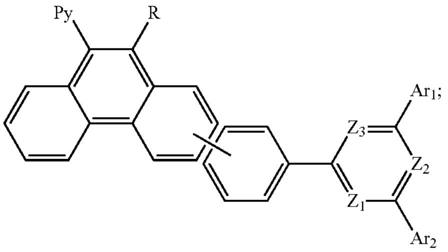

or;

I

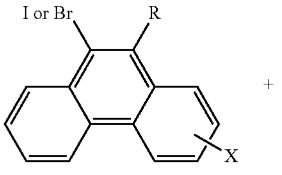

d

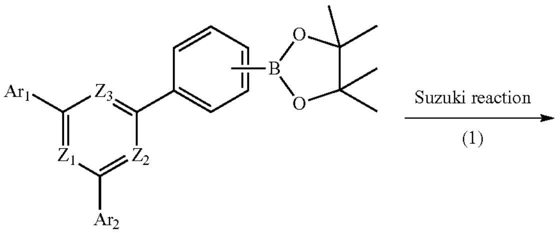

h

-continued

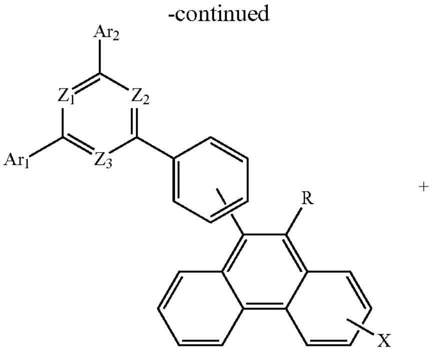

j

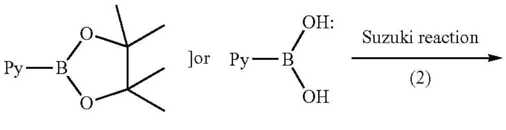

e

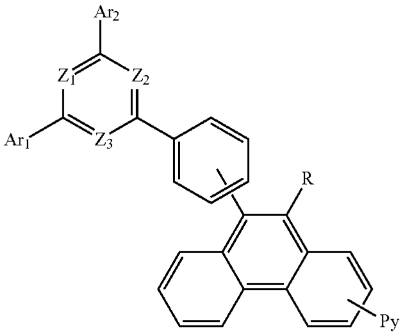

II wherein X=halogen.

6. An organic light-emitting device, wherein the organic light-emitting device comprises an anode, a cathode and an organic layer;

the organic layer comprises one or more than one of a light-emitting layer, a hole injection layer, a hole transport layer, a hole blocking layer, an electron injection layer or an electron transport layer; and at least one of the organic layer comprises the organic electronic material according to any one of claims 1-5.

7. The organic light-emitting device according to claim 6, wherein the light-emitting layer in the organic layer comprises the organic electronic material according to any one of claims 1-5.

8. The organic light-emitting device according to claim 6, wherein the electron transport layer or the electron injection layer in the organic layer comprises the organic electronic material according to any one of claims 1-5.

9. The organic light-emitting device according to claim 6, wherein the hole blocking layer in the organic layer comprises the organic electronic material according to any one of claims 1-5.

* * * * *